United States Patent
Tran

(10) Patent No.: US 8,673,572 B2
(45) Date of Patent: Mar. 18, 2014

(54) METHODS USED IN IDENTIFYING GLIOBLASTOMA

(75) Inventor: Nhan Tran, Phoenix, AZ (US)

(73) Assignee: The Translational Genomics Research Institute, Phoenix, AZ (US)

( * ) Notice: Subject to any disclaimer, the term of this patent is extended or adjusted under 35 U.S.C. 154(b) by 322 days.

(21) Appl. No.: 12/911,302

(22) Filed: Oct. 25, 2010

(65) Prior Publication Data

US 2012/0003209 A1 Jan. 5, 2012

Related U.S. Application Data

(60) Provisional application No. 61/254,624, filed on Oct. 23, 2009.

(51) Int. Cl.
*C12N 5/09* (2010.01)
*G01N 33/567* (2006.01)
*C07K 16/32* (2006.01)

(52) U.S. Cl.
USPC ....... 435/6.14; 435/330; 436/503; 530/391.1; 530/391.3

(58) Field of Classification Search
None
See application file for complete search history.

(56) References Cited

U.S. PATENT DOCUMENTS

2004/0106141 A1* 6/2004 Mischel et al. .................. 435/6

OTHER PUBLICATIONS

Elstrom et al., Akt Stimulates Aerobic Glycolysis in Cancer Cells, Cancer Res. 64, 3892-3899, 2004.*
Gao et al., PHLPP: a novel phosphatase that directly dephosphorylates Akt, promotes apoptosis and suppresses tumor growth. FASEB Journal, 19 (4), Suppl. S, Part 1, p. A258, 2005-Meeting abstract.*
Ruano et al., Identification of survival-related genes of the phosphatidylinositol 3- kinase signaling pathway in glioblastoma multiforme, Cancer, 112, 1575-1584, 2008.*
Ohgaki et al., Genetic pathways to primary and secondary glioblastoma, Am. J. Pathol. 170, 1445-1453, 2007.*
Furnari et al. , Malignant astrocytic glioma: genetics, biology, and paths to treatment, Genes & Dev. 21, 2683-2710, 2007.*
Holland E.C., Glioblastoma multiforme: The terminator, PNAS, 97, 6242-6244, 2000.*
Cell signalling AKT binding partners , Web accessed at http://www.cellsignal.com/reference/pathway/akt_binding.html on May 1, 2013.*

* cited by examiner

*Primary Examiner* — Elly-Gerald Stoica
(74) *Attorney, Agent, or Firm* — Rodney J. Fuller; Booth Udall Fuller PLC

(57) ABSTRACT

The invention encompasses methods and kits used in the identification of invasive glioblastoma based upon the expression of Akt1, Akt2, and Akt3. The methods and kits also allow prediction of disease outcome and staging of patients with regard to therapy.

14 Claims, 26 Drawing Sheets

SEQUENCE LISTING

<160> NUMBER OF SEQ ID NOS: 6

<210> SEQ ID NO 1
<211> LENGTH: 1443
<212> TYPE: DNA
<213> ORGANISM: Homo sapiens

<400> SEQUENCE: 1

```
atgagcgacg tggctattgt gaaggagggt tggctgcaca aacgagggga gtacatcaag      60
acctggcggc cacgctactt cctcctcaag aatgatggca ccttcattgg ctacaaggag     120
cggccgcagg atgtggacca acgtgaggct ccctcaaca acttctctgt ggcgcagtgc     180
cagctgatga agacggagcg gccccggccc aacaccttca tcatccgctg cctgcagtgg     240
accactgtca tcgaacgcac cttccatgtg gagactcctg aggagcggga ggagtggaca     300
accgccatcc agactgtggc tgacggcctc aagaagcagg aggaggagga gatggacttc     360
cggtcgggct cacccagtga caactcaggg gctgaagaga tggaggtgtc cctggccaag     420
cccaagcacc gcgtgaccat gaacgagttt gagtacctga agctgctggg caagggcact     480
ttcggcaagg tgatcctggt gaaggagaag gccacaggcc gctactacgc catgaagatc     540
ctcaagaagg aagtcatcgt ggccaaggac gaggtggccc acacactcac cgagaaccgc     600
gtcctgcaga actccaggca ccccttcctc acagccctga gtactctttt ccagacccac     660
gaccgcctct gctttgtcat ggagtacgcc aacggggcg agctgttctt ccacctgtcc     720
cgggaacgtg tgttctccga ggaccgggcc cgcttctatg gcgctgagat tgtgtcagcc     780
ctggactacc tgcactcgga gaagaacgtg gtgtaccggg acctcaagct ggagaacctc     840
atgctggaca aggacgggca cattaagatc acagacttcg ggctgtgcaa ggagggcatc     900
aaggacggtg ccaccatgaa gacctttgc ggcacacctg agtacctggc ccccgaggtg     960
ctggaggaca atgactacgg ccgtgcagtg gactggtggg gctgggcgt ggtcatgtac    1020 gagatgatgt gcggtcgcct gcccttctac aaccaggacc atgagaagct ttttgagctc    1080
atcctcatgg aggagatccg cttcccgcgc acgcttggtc ccgaggccaa gtccttgctt    1140
tcagggctgc tcaagaagga ccccaagcag aggcttggcg ggggctccga ggacgccaag    1200
gagatcatgc agcatcgctt cttgccggt atcgtgtggc agcacgtgta cgagaagaag    1260
ctcagcccac ccttcaagcc ccaggtcacg tcggagactg acaccaggta ttttgatgag    1320
gagttcacgg cccagatgat caccatcaca ccacctgacc aagatgacag catggagtgt    1380
gtggacagcg agcgcaggcc ccacttcccc cagttctcct actcggccag cagcacggcc    1440
tga                                                                  1443
```

<210> SEQ ID NO 2

```
<211> LENGTH: 480
<212> TYPE: PRT
<213> ORGANISM: Homo sapiens

<400> SEQUENCE: 2

Met Ser Asp Val Ala Ile Val Lys Glu Gly Trp Leu His Lys Arg Gly
1               5                   10                  15

Glu Tyr Ile Lys Thr Trp Arg Pro Arg Tyr Phe Leu Leu Lys Asn Asp
            20                  25                  30

Gly Thr Phe Ile Gly Tyr Lys Glu Arg Pro Gln Asp Val Asp Gln Arg
        35                  40                  45

Glu Ala Pro Leu Asn Asn Phe Ser Val Ala Gln Cys Gln Leu Met Lys
    50                  55                  60

Thr Glu Arg Pro Arg Pro Asn Thr Phe Ile Ile Arg Cys Leu Gln Trp
65                  70                  75                  80

Thr Thr Val Ile Glu Arg Thr Phe His Val Glu Thr Pro Glu Glu Arg
                85                  90                  95

Glu Glu Trp Thr Thr Ala Ile Gln Thr Val Ala Asp Gly Leu Lys Lys
            100                 105                 110

Gln Glu Glu Glu Met Asp Phe Arg Ser Gly Ser Pro Ser Asp Asn
        115                 120                 125

Ser Gly Ala Glu Glu Met Glu Val Ser Leu Ala Lys Pro Lys His Arg
    130                 135                 140

Val Thr Met Asn Glu Phe Glu Tyr Leu Lys Leu Leu Gly Lys Gly Thr
145                 150                 155                 160

Phe Gly Lys Val Ile Leu Val Lys Glu Lys Ala Thr Gly Arg Tyr Tyr
                165                 170                 175

Ala Met Lys Ile Leu Lys Lys Glu Val Ile Val Ala Lys Asp Glu Val
            180                 185                 190

Ala His Thr Leu Thr Glu Asn Arg Val Leu Gln Asn Ser Arg His Pro
        195                 200                 205

Phe Leu Thr Ala Leu Lys Tyr Ser Phe Gln Thr His Asp Arg Leu Cys
    210                 215                 220

Phe Val Met Glu Tyr Ala Asn Gly Gly Glu Leu Phe Phe His Leu Ser
225                 230                 235                 240

Arg Glu Arg Val Phe Ser Glu Asp Arg Ala Arg Phe Tyr Gly Ala Glu
                245                 250                 255

Ile Val Ser Ala Leu Asp Tyr Leu His Ser Glu Lys Asn Val Val Tyr
            260                 265                 270

Arg Asp Leu Lys Leu Glu Asn Leu Met Leu Asp Lys Asp Gly His Ile
        275                 280                 285

Lys Ile Thr Asp Phe Gly Leu Cys Lys Glu Gly Ile Lys Asp Gly Ala
    290                 295                 300

Thr Met Lys Thr Phe Cys Gly Thr Pro Glu Tyr Leu Ala Pro Glu Val
305                 310                 315                 320

Leu Glu Asp Asn Asp Tyr Gly Arg Ala Val Asp Trp Trp Gly Leu Gly
                325                 330                 335

Val Val Met Tyr Glu Met Met Cys Gly Arg Leu Pro Tyr Asn Gln
            340                 345                 350

Asp His Glu Lys Leu Phe Glu Leu Ile Leu Met Glu Glu Ile Arg Phe
        355                 360                 365

Pro Arg Thr Leu Gly Pro Glu Ala Lys Ser Leu Leu Ser Gly Leu Leu
    370                 375                 380

Lys Lys Asp Pro Lys Gln Arg Leu Gly Gly Gly Ser Glu Asp Ala Lys
385                 390                 395                 400
```

Glu Ile Met Gln His Arg Phe Phe Ala Gly Ile Val Trp Gln His Val
                405                 410                 415

Tyr Glu Lys Lys Leu Ser Pro Pro Phe Lys Pro Gln Val Thr Ser Glu
                420                 425                 430

Thr Asp Thr Arg Tyr Phe Asp Glu Glu Phe Thr Ala Gln Met Ile Thr
                435                 440                 445

Ile Thr Pro Pro Asp Gln Asp Asp Ser Met Glu Cys Val Asp Ser Glu
        450                 455                 460

Arg Arg Pro His Phe Pro Gln Phe Ser Tyr Ser Ala Ser Ser Thr Ala
465                 470                 475                 480

<210> SEQ ID NO 3
<211> LENGTH: 1317
<212> TYPE: DNA
<213> ORGANISM: Homo sapiens

<400> SEQUENCE: 3
atgaatgagg tgtctgtcat caaagaaggc tggctccaca agcgtggtga atacatcaag      60
acctggaggc cacggtactt cctgctgaag agcgacggct ccttcattgg gtacaaggag     120
aggcccgagg cccctgatca gactctaccc cccttaaaca acttctccgt agcagaatgc     180
cagctgatga agaccgagag gccgcgaccc aacacctttg tcatacgctg cctgcagtgg     240
accacagtca tcgagaggac cttccacgtg gattctccag acgagaggga ggagtggatg     300
cgggccatcc agatggtcgc caacagcctc aagcagcggg ccccaggcga ggaccccatg     360
gactacaagt gtggctcccc cagtgactcc tccacgactg aggagatgga agtggcggtc     420
agcaaggcac gggctaaagt gaccatgaat gacttcgact atctcaaact ccttggcaag     480
ggaacctttg gcaaagtcat cctggtgcgg gagaaggcca ctggccgcta ctacgccatg     540
aagatcctgc ggaaggaagt catcattgcc aaggatgaag tcgctcacac agtcaccgag     600
agccgggtcc tccagaacac caggcacccg ttcctcactg cgctgaagta tgccttccag     660
acccacgacc gcctgtgctt tgtgatggag tatgccaacg ggggtgagct gttcttccac     720
ctgtcccggg agcgtgtctt cacagaggag cgggcccggt tttatggtgc agagattgtc     780
tcggctcttg agtacttgca ctcgcgggac gtggtatacc gcgacatcaa ggtgctggag     840
gacaatgact atgccgggc cgtggactgg tgggggctgg tgtggtcat gtacgagatg     900 atgtgcggcc gcctgcccct ctacaaccag gaccacgagc gcctcttcga gctcatcctc     960
atggaagaga tccgcttccc gcgcacgctc agccccgagg ccaagtccct gcttgctggg    1020
ctgcttaaga aggaccccaa gcagaggctt ggtggggggc cagcgatgc aaggaggtc     1080 atggagcaca ggttcttcct cagcatcaac tggcaggacg tggtccagaa gaagctcctg    1140
ccacccttca aacctcaggt cacgtccgag gtcgacacaa ggtacttcga tgatgaattt    1200
accgcccagt ccatcacaat cacaccccct gaccgctatg acagcctggg cttactggag    1260
ctggaccagc ggaccccact cccccagttc tcctactcgg ccagcatccg cgagtga      1317

<210> SEQ ID NO 4
<211> LENGTH: 438
<212> TYPE: PRT
<213> ORGANISM: Homo sapiens

<400> SEQUENCE: 4

Met Asn Glu Val Ser Val Ile Lys Glu Gly Trp Leu His Lys Arg Gly
1               5                   10                  15

Glu Tyr Ile Lys Thr Trp Arg Pro Arg Tyr Phe Leu Leu Lys Ser Asp

-continued

```
                20                  25                  30
Gly Ser Phe Ile Gly Tyr Lys Glu Arg Pro Glu Ala Pro Asp Gln Thr
            35                  40                  45
Leu Pro Pro Leu Asn Asn Phe Ser Val Ala Glu Cys Gln Leu Met Lys
 50                  55                  60
Thr Glu Arg Pro Arg Pro Asn Thr Phe Val Ile Arg Cys Leu Gln Trp
 65                  70                  75                  80
Thr Thr Val Ile Glu Arg Thr Phe His Val Asp Ser Pro Asp Glu Arg
                85                  90                  95
Glu Glu Trp Met Arg Ala Ile Gln Met Val Ala Asn Ser Leu Lys Gln
            100                 105                 110
Arg Ala Pro Gly Glu Asp Pro Met Asp Tyr Lys Cys Gly Ser Pro Ser
            115                 120                 125
Asp Ser Ser Thr Thr Glu Glu Met Glu Val Ala Val Ser Lys Ala Arg
            130                 135                 140
Ala Lys Val Thr Met Asn Asp Phe Asp Tyr Leu Lys Leu Leu Gly Lys
145                 150                 155                 160
Gly Thr Phe Gly Lys Val Ile Leu Val Arg Glu Lys Ala Thr Gly Arg
                165                 170                 175
Tyr Tyr Ala Met Lys Ile Leu Arg Lys Glu Val Ile Ile Ala Lys Asp
                180                 185                 190
Glu Val Ala His Thr Val Thr Glu Ser Arg Val Leu Gln Asn Thr Arg
            195                 200                 205
His Pro Phe Leu Thr Ala Leu Lys Tyr Ala Phe Gln Thr His Asp Arg
            210                 215                 220
Leu Cys Phe Val Met Glu Tyr Ala Asn Gly Gly Glu Leu Phe Phe His
225                 230                 235                 240
Leu Ser Arg Glu Arg Val Phe Thr Glu Glu Arg Ala Arg Phe Tyr Gly
                245                 250                 255
Ala Glu Ile Val Ser Ala Leu Glu Tyr Leu His Ser Arg Asp Val Val
                260                 265                 270
Tyr Arg Asp Ile Lys Val Leu Glu Asp Asn Asp Tyr Gly Arg Ala Val
            275                 280                 285
Asp Trp Trp Gly Leu Gly Val Val Met Tyr Glu Met Met Cys Gly Arg
            290                 295                 300
Leu Pro Phe Tyr Asn Gln Asp His Glu Arg Leu Phe Glu Leu Ile Leu
305                 310                 315                 320
Met Glu Glu Ile Arg Phe Pro Arg Thr Leu Ser Pro Glu Ala Lys Ser
                325                 330                 335
Leu Leu Ala Gly Leu Leu Lys Lys Asp Pro Lys Gln Arg Leu Gly Gly
            340                 345                 350
Gly Pro Ser Asp Ala Lys Glu Val Met Glu His Arg Phe Phe Leu Ser
            355                 360                 365
Ile Asn Trp Gln Asp Val Val Gln Lys Lys Leu Leu Pro Pro Phe Lys
            370                 375                 380
Pro Gln Val Thr Ser Glu Val Asp Thr Arg Tyr Phe Asp Asp Glu Phe
385                 390                 395                 400
Thr Ala Gln Ser Ile Thr Ile Thr Pro Pro Asp Arg Tyr Asp Ser Leu
                405                 410                 415
Gly Leu Leu Glu Leu Asp Gln Arg Thr His Phe Pro Gln Phe Ser Tyr
            420                 425                 430
Ser Ala Ser Ile Arg Glu
            435
```

<210> SEQ ID NO 5
<211> LENGTH: 1399
<212> TYPE: DNA
<213> ORGANISM: Homo sapiens

<400> SEQUENCE: 5

```
atgagcgatg ttaccattgt gaaagaaggt tgggttcaga agaggggaga atatataaaa      60
aactggaggc caagatactt ccttttgaag acagatggct cattcatagg atataaagag     120
aaacctcaag atgtggaatt acctcatccc ctcaaccact tttcagtggc aaaatgccag     180
ttaacgaaaa caagacgacc aaagccaaac acatttataa tcagatgtct ccagtggact     240
actgttatag agagaacatt tcatgtagat actccagagg aaagggaaga atggacagaa     300
gctatccagg ctgtagcaga cagactgcag aggcaagaag aggagagaat gaattgtagt     360
ccaacttcac aaattgataa tataggagag aagagatgg atgcctctac aacccatcat     420
aaaagaaaga caatgaatga ttttgactat ttgaaactac taggtaaagg cacttttggg     480
aaagttattt tggttcgaga gaaggcaagt ggaaaatact atgctatgaa gattctgaag     540
aaagaagtca ttattgcaaa ggatgaagtg gcacacactc taactgaaag cagagtatta     600
aagaacacta gacatccctt tttaacatcc ttgaaatatt ccttccagac aaaagaccgt     660
ttgtgttttg tgatggaata tgttaatggg ggcgagctgt ttttccattt gtcgagagag     720
cgggtgttct ctgaggaccg cacacgtttc tatggtgcag aaattgtctc tgccttggac     780
tatctacatt ccggaaagat tgtgtaccgt gatctcaagt gggagaatct aatgctggac     840
aaagatggcc acataaaaat tacagatttt ggactttgca agaagggat cacagatgca     900
gccaccatga agacattctg tggcactcca gaatatctgg caccagaggt gttagaagat     960
aatgactatg gccgagcagt agactggtgg ggcctagggg ttgtcatgta tgaaatgatg    1020
tgtgggaggt tacctttcta caaccaggac catgagaaac tttttgaatt aatattaatg    1080
gaagacatta aatttcctcg aacactctct tcagatgcaa atcattgct ttcagggctc    1140
ttgataaagg atccaaataa acgccttggt ggaggaccag atgatgcaaa agaaattatg    1200
agacacagtt tcttctctgg agtaaactgg caagatgtat atgataaaaa gcttgtacct    1260
ccttttaaac ctcaagtaac atctgagaca gatactagat attttgatga agaatttaca    1320
gctcagacta ttcaataac accacctgaa aaatatgatg aggatggtat ggactgcatg    1380
gacaatgaga ggcggccgc                                                1399
```

<210> SEQ ID NO 6
<211> LENGTH: 466
<212> TYPE: PRT
<213> ORGANISM: Homo sapiens

<400> SEQUENCE: 6

Met Ser Asp Val Thr Ile Val Lys Glu Gly Trp Val Gln Lys Arg Gly
1               5                   10                  15

Glu Tyr Ile Lys Asn Trp Arg Pro Arg Tyr Phe Leu Leu Lys Thr Asp
            20                  25                  30

Gly Ser Phe Ile Gly Tyr Lys Glu Lys Pro Gln Asp Val Glu Leu Pro
        35                  40                  45

His Pro Leu Asn His Phe Ser Val Ala Lys Cys Gln Leu Thr Lys Thr
    50                  55                  60

Arg Arg Pro Lys Pro Asn Thr Phe Ile Ile Arg Cys Leu Gln Trp Thr
65                  70                  75                  80

Thr Val Ile Glu Arg Thr Phe His Val Asp Thr Pro Glu Glu Arg Glu

```
                    85                  90                  95
Glu Trp Thr Glu Ala Ile Gln Ala Val Ala Asp Arg Leu Gln Arg Gln
                100                 105                 110

Glu Glu Glu Arg Met Asn Cys Ser Pro Thr Ser Gln Ile Asp Asn Ile
                115                 120                 125

Gly Glu Glu Glu Met Asp Ala Ser Thr Thr His His Lys Arg Lys Thr
130                 135                 140

Met Asn Asp Phe Asp Tyr Leu Lys Leu Leu Gly Lys Gly Thr Phe Gly
145                 150                 155                 160

Lys Val Ile Leu Val Arg Glu Lys Ala Ser Gly Lys Tyr Tyr Ala Met
                165                 170                 175

Lys Ile Leu Lys Lys Glu Val Ile Ile Ala Lys Asp Glu Val Ala His
                180                 185                 190

Thr Leu Thr Glu Ser Arg Val Leu Lys Asn Thr Arg His Pro Phe Leu
                195                 200                 205

Thr Ser Leu Lys Tyr Ser Phe Gln Thr Lys Asp Arg Leu Cys Phe Val
                210                 215                 220

Met Glu Tyr Val Asn Gly Gly Glu Leu Phe Phe His Leu Ser Arg Glu
225                 230                 235                 240

Arg Val Phe Ser Glu Asp Arg Thr Arg Phe Tyr Gly Ala Glu Ile Val
                245                 250                 255

Ser Ala Leu Asp Tyr Leu His Ser Gly Lys Ile Val Tyr Arg Asp Leu
                260                 265                 270

Lys Leu Glu Asn Leu Met Leu Asp Lys Asp Gly His Ile Lys Ile Thr
                275                 280                 285

Asp Phe Gly Leu Cys Lys Glu Gly Ile Thr Asp Ala Ala Thr Met Lys
                290                 295                 300

Thr Phe Cys Gly Thr Pro Glu Tyr Leu Ala Pro Glu Val Leu Glu Asp
305                 310                 315                 320

Asn Asp Tyr Gly Arg Ala Val Asp Trp Trp Gly Leu Gly Val Val Met
                325                 330                 335

Tyr Glu Met Met Cys Gly Arg Leu Pro Phe Tyr Asn Gln Asp His Glu
                340                 345                 350

Lys Leu Phe Glu Leu Ile Leu Met Glu Asp Ile Lys Phe Pro Arg Thr
                355                 360                 365

Leu Ser Ser Asp Ala Lys Ser Leu Leu Ser Gly Leu Leu Ile Lys Asp
                370                 375                 380

Pro Asn Lys Arg Leu Gly Gly Pro Asp Asp Ala Lys Glu Ile Met
385                 390                 395                 400

Arg His Ser Phe Phe Ser Gly Val Asn Trp Gln Asp Val Tyr Asp Lys
                405                 410                 415

Lys Leu Val Pro Pro Phe Lys Pro Gln Val Thr Ser Glu Thr Asp Thr
                420                 425                 430

Arg Tyr Phe Asp Glu Glu Phe Thr Ala Gln Thr Ile Thr Ile Thr Pro
                435                 440                 445

Pro Glu Lys Tyr Asp Glu Asp Gly Met Asp Cys Met Asp Asn Glu Arg
                450                 455                 460

Arg Pro
465
```

METHODS USED IN IDENTIFYING GLIOBLASTOMA

PRIORITY CLAIM

This application claims the benefit of U.S. Provisional Application No. 61/254,624, filed 23 Oct. 2009, hereby incorporated by reference in its entirety.

BACKGROUND OF THE INVENTION

Glioblastoma multiforme (GBM) is the most malignant form of all primary adult brain tumors (See Reference 1). Although significant technical advances in surgical and radiation treatment for brain tumors have emerged, their impact on clinical outcome for patients has been disappointing (See References 2-4). Of the features that characterize GBM, none is more clinically significant than the capacity of glioma cells to infiltrate into normal brain tissue (See Reference 5). These invasive cells render tumor resection ineffective, and confer resistance to chemo- and radiation-therapy. Tests that identify invasive glioblastoma are necessary for purposes such as prediction of disease outcome and prediction of treatment effectiveness.

BRIEF SUMMARY OF THE INVENTION

The present invention provides among other things:

It is an object of the invention to detect invasive glioblastoma in a subject.

It is an object of the invention to visualize invasive glioblastoma cells.

It is an object of the invention to select a treatment on the basis of the presence of invasive glioblastoma.

It is an object of the invention to identify patients likely to respond to new classes of glioblastoma therapeutics.

The above and other objects may be achieved through the use of methods involving, adding a first reagent capable of binding to a marker selected from the group consisting of SEQ ID NO. 1, SEQ ID NO. 2, SEQ ID NO. 3, SEQ ID NO. 4, SEQ ID NO. 5, and SEQ ID NO. 6 to a mixture comprising a tumor sample; subjecting the mixture to conditions that allow detection of the binding of the reagent to the marker; and classifying the tumor into a cohort selected from the group consisting of invasive glioblastoma and proliferative glioblastoma on the basis of a result of the binding of the reagent to the sample. In some aspects of the invention, the marker includes a sequence selected from the group consisting of SEQ ID NO. 2, SEQ ID NO. 4, and SEQ ID NO. 6. In those aspects, the first reagent may comprise a first antibody. The first antibody may comprise a first label. The first label may be any label, such as a fluorescent compound, an enzyme, a radioisotope, or a ligand. The method may further comprise adding to the mixture a second antibody capable of binding to the first antibody. The second antibody may comprise a second label. The second label may be any label such as a fluorescent compound, an enzyme, a radioisotope, or a ligand.

In other aspects of the invention, the marker may include a sequence selected from the group consisting of SEQ ID NO. 1, SEQ ID NO. 3, and SEQ ID NO. 5. In those other aspects, the first reagent may comprise a first nucleic acid and the first nucleic acid may further comprise a first oligonucleotide capable of binding to part of the marker. The method may further comprise purifying RNA from the sample, performing reverse transcription on the RNA, adding a second oligonucleotide capable of binding to part of the marker to the mixture, wherein the conditions comprise subjecting the mixture to nucleic acid amplification, wherein the first oligonucleotide and the second oligonucleotide are capable of binding to different sequences on the marker, and wherein the first oligonucleotide and the second oligonucleotide are capable of binding to separate nucleic acid strands. The method may further comprise adding a third oligonucleotide to the mixture, wherein the third oligonucleotide is capable of binding to part of the marker between the sequences to which the first oligonucleotide and the second oligonucleotide are capable of binding. The third oligonucleotide may comprise a fluorescent compound. The fluorescent compound may be any fluorescent compound including a compound selected from the group consisting of FAM, dR110, 5-FAM, 6FAM, dR6G, JOE, HEX, VIC, TET, dTAMRA, TAMRA, NED, dROX, PET, BHQ+, Gold540, and LIZ. The method may comprise performing DNA sequencing on a product of the nucleic acid amplification. In some aspects of the invention, the first reagent may be affixed to a solid substrate. In those aspects, the conditions may comprise microarray analysis. The sample may be any sample such as a sample that comprises a cell. One example of such a sample is a brain biopsy sample.

The above and other objects may be achieved through the use of methods involving adding a first reagent capable of binding to a marker selected from the group consisting of SEQ ID NO. 1, SEQ ID NO. 2, SEQ ID NO. 3, SEQ ID NO. 4, SEQ ID NO. 5, and SEQ ID NO. 6 to a mixture comprising a tumor sample from a patient, subjecting the mixture to conditions that allow detection of the binding of the reagent to the marker, and classifying the patient into a cohort selected from the group consisting of short term survivors and long term survivors. If the marker is selected from the group consisting of SEQ ID NO. 1, SEQ ID NO. 2, SEQ ID NO. 3, and SEQ ID NO. 4, the binding of the reagent may be above a threshold and the patient classified into short-term survivors. If the marker is selected from the group consisting of SEQ ID NO. 5 and SEQ ID NO. 6, then the binding of the reagent may be above a threshold and the patient classified into long-term survivors. The short term survivors may be predicted to survive less than 680 days from biopsy including less than 400 days from biopsy. The long term survivors may be predicted to survive more than 680 days from biopsy, including more than 950 days from biopsy.

The above and other objects may be achieved through the use of methods involving: adding a first reagent capable of binding to a marker selected from a group consisting of SEQ ID NO. 1, SEQ ID NO. 2, SEQ ID NO. 3, SEQ ID NO. 4, SEQ ID NO. 5, and SEQ ID NO. 6 to a mixture comprising a sample, subjecting the mixture to conditions that allow detection of the binding of the reagent to the marker, and treating the patient on the basis of a result of the binding of the reagent to the sample. If the marker includes SEQ ID NO. 1, SEQ ID NO. 2, SEQ ID NO. 3, or SEQ ID NO. 4 and the result comprises expression below a threshold level, then treating the patient may comprise administering a therapeutic composition comprising a compound selected from the group consisting of temozolimide and bevacizumab. If the marker includes SEQ ID NO. 5 or SEQ ID NO. 6 and the result comprises expression above a threshold level, then treating the patient may comprise administering a therapeutic composition comprising a compound selected from the group consisting of temozolimide and bevacizumab. If the marker is selected from the group consisting of SEQ ID NO. 1, SEQ ID NO. 2, SEQ ID NO. 3 or SEQ ID NO. 4 and the result comprises expression above a threshold level, then treating the patient may comprise administering a therapeutic composition comprising a drug selected from the group consisting of TROY inhibitor, Pyk2 inhibitor, Rac1 inhibitor, Dock180 inhibitor, Dock7 inhibitor, TWEAK inhibitor, Fn14 inhibitor, BAD inhibitor, and PI3K inhibitor.

The above and other objects may be achieved through the use of kits involving a first reagent capable of specific binding to a marker selected from the group consisting of SEQ ID NO. 1, SEQ ID NO. 2, SEQ ID NO. 3, SEQ ID NO. 4, SEQ ID NO. 5, and SEQ ID NO. 6 and an indication of a result, wherein the result signifies that the tumor is an invasive glioblastoma. The first reagent may comprise a first antibody. The first antibody may comprise a first label. The first label may be any label such as a fluorescent compound, an enzyme, a radioisotope, or a ligand. The kit may further comprise a second antibody capable of binding to the first antibody. The second antibody may comprise a second label. The second label may be any label such as a fluorescent compound, an enzyme, a radioisotope, or a ligand. The first reagent may comprise a first nucleic acid. The first nucleic acid may comprise a first oligonucleotide capable of binding to part of the marker. The kit may further comprise a second oligonucleotide capable of binding to part of the marker wherein the first oligonucleotide and the second oligonucleotide are capable of binding to different sequences on the marker and wherein the first oligonucleotide and the second oligonucleotide are capable of binding to separate nucleic acid strands. The kit may further comprise a third nucleotide wherein the third nucleotide binds to part of the marker between the sequences to which the first oligonucleotide and the second oligonucleotide are capable of binding. The third nucleic acid may comprise a fluorescent compound. The florescent compound may be any fluorescent compound including dR110, 5-FAM, 6FAM, dR6G, JOE, HEX, VIC, TET, dTAMRA, TAMRA, NED, dROX, PET, BHQ+, Gold540, and LIZ. The kit may further comprise an enzyme. The enzyme may be any enzyme such as a DNA polymerase or a reverse transcriptase. The first reagent may be affixed to a solid substrate. The indication may be any indication, such as a positive control or a writing. A writing may be made available via a website, or it may include a photograph. The indication may be physically included in the kit. The indication may comprise software configured to detect a level of expression as input and identification of invasive glioblastoma as output. The software may be incorporated into a machine configured to detect binding of the reagent to the marker.

BRIEF DESCRIPTION OF THE FIGURES

A more complete understanding of the present invention may be derived by referring to the detailed description when considered in connection with the following illustrative figures.

Figure 1:
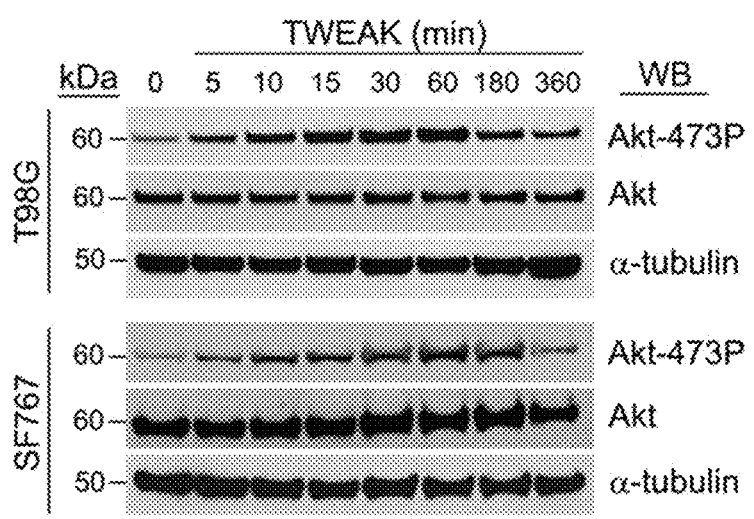
FIG. 1 depicts lysates of T98G and SF767 gliomal cells treated with TWEAK and western blotted for total and phosphorylated Akt.

Elements and acts in the figures are illustrated for simplicity and have not necessarily been rendered according to any particular sequence or embodiment.

DETAILED DESCRIPTION OF THE INVENTION

In the following description, and for the purposes of explanation, numerous specific details are set forth in order to provide a thorough understanding of the various aspects of the invention. It will be understood, however, by those skilled in the relevant arts, that the present invention may be practiced without these specific details. In other instances, known structures and devices are shown or discussed more generally in order to avoid obscuring the invention.

Gliomas, primary brain tumors that derive from glial support cells, are the most common primary tumor of the adult central nervous system and will result in an estimated 13,000 deaths in 2010. Adult gliomas of astrocytic origin (astrocytomas) comprise a spectrum of neoplasms that are generally classified by WHO standards into low-grade benign tumors (i.e. juvenile pilocytic astrocytoma, diffuse astrocytoma) and high-grade malignant tumors (i.e. anaplastic astrocytoma and glioblastoma multiforme; GBM). Patients diagnosed with grade IV GBM, the most aggressive malignant glioma, have a median survival of 9-12 months after the onset of clinical symptoms. Molecular analyses of glioma specimens have identified several common genetic alterations (e.g., p16INK4a deletion) and gene expression changes (e.g., EGFR overexpression) that may contribute to glioblastoma formation.

In general, gliomas are extremely difficult to treat using conventional approaches. This is primarily due to the intrinsic propensity of glioma cells to exit the tumor core and invade the adjacent normal brain parenchyma. These migrating cells escape surgical resection and are poorly targeted by radiation or chemotherapy. They sometimes travel over long distances, frequently along blood vessel and fiber tracts, and then initiate secondary tumor growth at their final destination. This distinguishing invasive ability is not shared by nonglial cells that metastasize from other primary tumor sites (e.g. breast) to brain tissue. The invasion of glioma cells is likely triggered by a presently undefined signal or signals that promote a cascade of cellular responses, including cell elongation, integrin-mediated cell attachment to extracellular matrix (ECM) molecules, the production and secretion of ECM-degrading enzymes, and cell movement.

Migrating glioma cells exhibit decreased susceptibility to pro-apoptotic agents providing them with an additional mechanism for resisting current radiological and chemotherapeutic treatment modalities.

Herein, the Inventor demonstrates that Akt1, Akt2, and Akt3 serve as markers of invasive glioblastoma, resistance to temozolimide and avastin and as markers of sensitivity to classes of drugs that treat glioblastoma by targeting pathways that contribute to glioma cell migration and invasion.

A marker may be any molecular structure produced by a cell, expressed inside the cell, accessible on the cell surface, or secreted by the cell. A marker may be any protein, carbohydrate, fat, nucleic acid, catalytic site, or any combination of these such as an enzyme, glycoprotein, cell membrane, virus, cell, organ, organelle, or any uni- or multimolecular structure or any other such structure now known or yet to be disclosed whether alone or in combination. A marker may also be called a target and the terms are used interchangeably.

A marker may be represented by the sequence of a nucleic acid from which it can be derived. Examples of such nucleic acids include miRNA, tRNA, siRNA, mRNA, cDNA, or genomic DNA sequences. While a marker may be represented by the sequence of a single nucleic acid strand (e.g. 5'→3'), nucleic acid reagents that bind the marker may also bind to the complementary strand (e.g. 3'→5'). Alternatively, a marker may be represented by a protein sequence. The concept of a marker is not limited to the products of the exact nucleic acid sequence or protein sequence by which it may be represented. Rather, a marker encompasses all molecules that may be detected by a method of assessing the expression of the marker.

Examples of molecules encompassed by a marker include point mutations, silent mutations, deletions, frameshift mutations, translocations, alternative splicing derivatives, differentially methylated sequences, differentially modified protein sequences, truncations, soluble forms of cell membrane associated markers, and any other variation that results in a product that may be identified as the marker. The following nonlimiting examples are included for the purposes of clarifying this concept: If expression of a specific marker in a sample is assessed by RTPCR, and if the sample expresses an mRNA sequence different from the sequence used to identify the specific marker by one or more nucleotides, but the marker may still be detected using RTPCR, then the specific marker encompasses the sequence present in the sample. Alternatively if expression of a specific marker in a sample is assessed by an antibody and the amino acid sequence of the marker in the sample differs from a sequence used to identify marker by one or more amino acids, but the antibody is still able to bind to the version of the marker in the sample, then the specific marker encompasses the sequence present in the sample.

Expression encompasses any and all processes through which material derived from a nucleic acid template may be produced. Expression thus includes processes such as RNA transcription, mRNA splicing, protein translation, protein folding, post-translational modification, membrane transport, associations with other molecules, addition of carbohydrate moeties to proteins, phosphorylation, protein complex formation and any other process along a continuum that results in biological material derived from genetic material whether in vitro, in vivo, or ex vivo. Expression also encompasses all processes through which the production of material derived from a nucleic acid template may be actively or passively suppressed. Such processes include all aspects of transcriptional and translational regulation. Examples include heterochromatic silencing, differential methylation, transcription factor inhibition, any form of RNAi silencing, microRNA silencing, alternative splicing, protease digestion, posttranslational modification, and alternative protein folding.

Expression may be assessed by any number of methods used to detect material derived from a nucleic acid template used currently in the art and yet to be developed. Examples of such methods include any nucleic acid detection method including the following nonlimiting examples, microarray analysis, RNA in situ hybridization, RNAse protection assay, Northern blot, reverse transcriptase PCR, quantitative PCR, quantitative reverse transcriptase PCR, quantitative real-time reverse transcriptase PCR, reverse transcriptase treatment followed by direct sequencing, direct sequencing of genomic DNA, or any other method of detecting a specific nucleic acid now known or yet to be disclosed. Other examples include any process of assessing protein expression including flow cytometry, immunohistochemistry, ELISA, Western blot, and immunoaffinity chromatograpy, HPLC, mass spectrometry, protein microarray analysis, PAGE analysis, isoelectric focusing, 2-D gel electrophoresis, or any enzymatic assay. Methods of detecting expression may include methods of purifying nucleic acid, protein, or some other material depending on the type of marker. Any method of nucleic acid purification may be used, depending on the type of marker. Examples include phenol alcohol extraction, ethanol extraction, guanidium isothionate extraction, gel purification, size exclusion chromatography, cesium chloride preparations, and silica resin preparation. Any method of protein purification may be used, also depending on the type of marker. Examples include size exclusion chromatography, hydrophobic interaction chromatography, ion exchange chromatograpy, affinity chromatograpy (including affinity chromatograpy of tagged proteins), metal binding, immunoaffinity chromatography, and HPLC.

Nucleic acid amplification is a process by which copies of a nucleic acid may be made from a source nucleic acid. Nucleic acids that may be subjected to amplification may be from any source. In some nucleic amplification methods, the copies are generated exponentially. Examples of nucleic acid amplification include but are not limited to: the polymerase chain reaction (PCR), ligase chain reaction (LCR,) self-sustained sequence replication (3SR), nucleic acid sequence based amplification (NASBA,) strand displacement amplification (SDA,) amplification with Qβ replicase, whole genome amplification with enzymes such as φ29, whole genome PCR, in vitro transcription with any RNA polymerase, or any other method by which copies of a desired sequence are generated.

Polymerase chain reaction (PCR) is a particular method of amplifying DNA, generally involving the mixing of a nucleic sample, two or more primers, a DNA polymerase, which may be a thermostable DNA polymerase such as Taq or Pfu, and deoxyribose nucleoside triphosphates (dNTP's). In general, the reaction mixture is subjected to temperature cycles comprising a denaturation stage, (typically 80-100° C.) an annealing stage with a temperature that is selected based on the melting temperature (Tm) of the primers and the degeneracy of the primers, and an extension stage (for example 40-75° C.) In real-time PCR analysis, additional reagents, methods, optical detection systems, and devices are used that allow a measurement of the magnitude of fluorescence in proportion to concentration of amplified DNA. In such analyses, incorporation of fluorescent dye into the amplified strands may be detected or labeled probes that bind to a specific sequence during the annealing phase release their fluorescent tags during the extension phase. Either of these will allow a quantification of the amount of specific DNA present in the initial sample. Often, the result of a real-time PCR will be expressed in the terms of cycle threshold (Ct) values. The Ct represents the number of PCR cycles for the fluorescent signal from a real-time PCR reaction to cross a threshold value of fluorescence. Ct is inversely proportional to the amount of target nucleic acid originally present in the sample. RNA may be detected by PCR analysis by creating a DNA template from RNA through a reverse transcriptase enzyme.

Other methods used to assess expression include the use of natural or artificial ligands capable of specifically binding a marker. Such ligands include antibodies, antibody complexes, conjugates, natural ligands, small molecules, nanoparticles, or any other molecular entity capable of specific binding to a marker. Antibodies may be monoclonal, polyclonal, or any antibody fragment including an Fab, F(ab)$_2$, Fv, scFv, phage display antibody, peptibody, multispecific ligand, or any other reagent with specific binding to a marker. Ligands may be associated with a label such as a radioactive isotope or chelate thereof, dye (fluorescent or nonfluorescent,) stain, enzyme, metal, or any other substance capable of aiding a machine or a human eye from differentiating a cell expressing a marker from a cell not expressing a marker. Additionally, expression may be assessed by monomeric or multimeric ligands associated with substances capable of killing the cell. Such substances include protein or small molecule toxins, cytokines, pro-apoptotic substances, pore forming substances, radioactive isotopes, or any other substance capable of killing a cell.

Differential expression encompasses any detectable difference between the expression of a marker in one sample relative to the expression of the marker in another sample. Differential expression may be assessed by a detector, an instrument containing a detector, or by aided or unaided human eye. Examples include but are not limited to differential staining of cells in an IHC assay configured to detect a marker, differential detection of bound RNA on a microarray to which a sequence capable of binding to the marker is bound, differential results in measuring RTPCR measured in the number of PCR cycles necessary to reach a particular optical density at a wavelength at which a double stranded DNA binding dye (e.g. SYBR Green) incorporates, differential results in measuring label from a reporter probe used in a real-time RTPCR reaction, differential detection of fluorescence on cells using a flow cytometer, differential intensities of bands in a Northern blot, differential intensities of bands in an RNAse protection assay, differential cell death measured by apoptotic markers, differential cell death measured by shrinkage of a tumor, or any method that allows a detection of a difference in signal between one sample or set of samples and another sample or set of samples.

The expression of the marker in a sample may be compared to a level of expression predetermined to predict the presence or absence of a particular physiological characteristic. The level of expression may be derived from a single control or a set of controls. A control may be any sample with a previously determined level of expression. A control may comprise material within the sample or material from sources other than the sample. Alternatively, the expression of a marker in a sample may be compared to a control that has a level of expression predetermined to signal or not signal a cellular or physiological characteristic. This level of expression may be derived from a single source of material including the sample itself or from a set of sources. Comparison of the expression of the marker in the sample to a particular level of expression results in a prediction that the sample exhibits or does not exhibit the cellular or physiological characteristic.

Prediction of a cellular or physiological characteristic includes the prediction of any cellular or physiological state that may be predicted by assessing the expression of a marker. Examples include the identity of a cell as a particular cell including a particular normal or cancer cell type, the likelihood that one or more diseases is present or absent, the likelihood that a present disease will progress, remain unchanged, or regress, the likelihood that a disease will respond or not respond to a particular therapy, or any other outcome. Further examples include the likelihood that a cell will move, senesce, apoptose, differentiate, metastasize, or change from any state to any other state or maintain its current state.

Expression of a marker in a sample may be more or less than that of a level predetermined to predict the presence or absence of a cellular or physiological characteristic. The expression of the marker in the sample may be more than 1,000,000×, 100,000×, 10,000×, 1000×, 100×, 10×, 5×, 2×, 1×, 0.5×, 0.1×0.01×, 0.001×, 0.0001×, 0.00001×, 0.000001×, 0.0000001× or less than that of a level predetermined to predict the presence or absence of a cellular or physiological characteristic.

The invention contemplates assessing the expression of the marker in any biological sample from which the expression may be assessed. One skilled in the art would know to select a particular biological sample and how to collect said sample depending upon the marker that is being assessed. Examples of sources of samples include but are not limited to biopsy or other in vivo or ex vivo analysis of prostate, breast, skin, muscle, facia, brain, endometrium, lung, head and neck, pancreas, small intestine, blood, liver, testes, ovaries, colon, skin, stomach, esophagus, spleen, lymph node, bone marrow, kidney, placenta, or fetus. In some aspects of the invention, the sample comprises a fluid sample, such as peripheral blood, lymph fluid, ascites, serous fluid, pleural effusion, sputum, cerebrospinal fluid, amniotic fluid, lacrimal fluid, stool, or urine. Samples include single cells, whole organs or any fraction of a whole organ, in any condition including in vitro, ex vivo, in vivo, post-mortem, fresh, fixed, or frozen.

One type of cellular or physiological characteristic is the risk that a particular disease outcome will occur. Assessing this risk includes the performing of any type of test, assay, examination, result, readout, or interpretation that correlates with an increased or decreased probability that an individual has had, currently has, or will develop a particular disease, disorder, symptom, syndrome, or any condition related to health or bodily state. Examples of disease outcomes include, but need not be limited to survival, death, progression of existing disease, remission of existing disease, initiation of onset of a disease in an otherwise disease-free subject, or the continued lack of disease in a subject in which there has been a remission of disease. Assessing the risk of a particular disease encompasses diagnosis in which the type of disease afflicting a subject is determined. Assessing the risk of a disease outcome also encompasses the concept of prognosis. A prognosis may be any assessment of the risk of disease outcome in an individual in which a particular disease has been diagnosed. Assessing the risk further encompasses prediction of therapeutic response in which a treatment regimen is chosen based on the assessment. Assessing the risk also encompasses a prediction of overall survival after diagnosis.

Determining the level of expression that signifies a physiological or cellular characteristic may be assessed by any of a number of methods. The skilled artisan will understand that numerous methods may be used to select a level of expression for a particular marker or a plurality of markers that signifies a particular physiological or cellular characteristics. In diagnosing the presence of a disease, a threshold value may be obtained by performing the assay method on samples obtained from a population of patients having a certain type of disease (cancer for example,) and from a second population of subjects that do not have the disease. In assessing disease outcome or the effect of treatment, a population of patients, all of which have, a disease such as cancer, may be followed for a period of time. After the period of time expires, the population may be divided into two or more groups. For example, the population may be divided into a first group of patients whose disease progresses to a particular endpoint and a second group of patients whose disease does not progress to the particular endpoint. Examples of endpoints include disease recurrence, death, metastasis or other states to which disease may progress. If expression of the marker in a sample is more similar to the predetermined expression of the marker in one group relative to the other group, the sample may be assigned a risk of having the same outcome as the patient group to which it is more similar.

In addition, one or more levels of expression of the marker may be selected that signify a particular physiological or cellular characteristic. For example, Receiver Operating Characteristic curves, or "ROC" curves, may be calculated by plotting the value of a variable versus its relative frequency in two populations. For any particular marker, a distribution of marker expression levels for subjects with and without a disease may overlap. This indicates that the test does not absolutely distinguish between the two populations with complete accuracy. The area of overlap indicates where the test cannot distinguish the two groups. A threshold is selected. Expression of the marker in the sample above the threshold indicates the sample is similar to one group and expression of the marker below the threshold indicates the sample is similar to the other group. The area under the ROC curve is a measure of the probability that the expression correctly indicated the similarity of the sample to the proper group. See, e.g., Hanley et al., Radiology 143: 29-36 (1982) hereby incorporated by reference.

Additionally, levels of expression may be established by assessing the expression of a marker in a sample from one patient, assessing the expression of additional samples from the same patient obtained later in time, and comparing the expression of the marker from the later samples with the initial sample or samples. This method may be used in the case of markers that indicate, for example, progression or worsening of disease or lack of efficacy of a treatment regimen or remission of a disease or efficacy of a treatment regimen.

Other methods may be used to assess how accurately the expression of a marker signifies a particular physiological or cellular characteristic. Such methods include a positive likelihood ratio, negative likelihood ratio, odds ratio, and/or hazard ratio. In the case of a likelihood ratio, the likelihood that the expression of the marker would be found in a sample with a particular cellular or physiological characteristic is compared with the likelihood that the expression of the marker would be found in a sample lacking the particular cellular or physiological characteristic.

An odds ratio measures effect size and describes the amount of association or non-independence between two groups. An odds ratio is the ratio of the odds of a marker being expressed in one set of samples versus the odds of the marker being expressed in the other set of samples. An odds ratio of 1 indicates that the event or condition is equally likely to occur in both groups. An odds ratio grater or less than 1 indicates that expression of the marker is more likely to occur in one group or the other depending on how the odds ratio calculation was set up.

A hazard ratio may be calculated by estimate of relative risk. Relative risk is the chance that a particular event will take place. It is a ratio of the probability that an event such as development or progression of a disease will occur in samples that exceed a threshold level of expression of a marker over the probability that the event will occur in samples that do not exceed a threshold level of expression of a marker. Alternatively, a hazard ratio may be calculated by the limit of the number of events per unit time divided by the number at risk as the time interval decreases. In the case of a hazard ratio, a value of 1 indicates that the relative risk is equal in both the first and second groups. A value greater or less than 1 indicates that the risk is greater in one group or another, depending on the inputs into the calculation.

Additionally, multiple threshold levels of expression may be determined. This can be the case in so-called "tertile," "quartile," or "quintile" analyses. In these methods, multiple groups can be considered together as a single population, and are divided into 3 or more bins having equal numbers of individuals. The boundary between two of these "bins" may be considered threshold levels of expression indicating a particular level of risk of a disease developing or signifying a physiological or cellular state. A risk may be assigned based on which "bin" a test subject falls into.

A subject includes any human or non-human mammal, including for example: a primate, cow, horse, pig, sheep, goat, dog, cat, or rodent, capable of developing cancer including human patients that are suspected of having cancer, that have been diagnosed with cancer, or that have a family history of cancer. Methods of identifying subjects suspected of having cancer include but are not limited to: physical examination, family medical history, subject medical history including exposure to environmental factors, biopsy, or any of a number of imaging technologies such as ultrasonography, computed tomography, magnetic resonance imaging, magnetic resonance spectroscopy, or positron emission tomography.

Cancer cells include any cells derived from a tumor, neoplasm, cancer, precancer, cell line, malignancy, or any other source of cells that have the potential to expand and grow to an unlimited degree. Cancer cells may be derived from naturally occurring sources or may be artificially created. Cancer cells may also be capable of invasion into other tissues and metastasis. Cancer cells further encompass any malignant cells that have invaded other tissues and/or metastasized. One or more cancer cells in the context of an organism may also be called a cancer, tumor, neoplasm, growth, malignancy, or any other term used in the art to describe cells in a cancerous state.

Examples of cancers that could serve as sources of cancer cells include solid tumors such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma.

Additional cancers that may serve as sources of cancer cells include blood borne cancers such as acute lymphoblastic leukemia ("ALL,"), acute lymphoblastic B-cell leukemia, acute lymphoblastic T-cell leukemia, acute myeloblastic leukemia ("AML"), acute promyelocytic leukemia ("APL"), acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia ("CML"), chronic lymphocytic leukemia ("CLL"), hairy cell leukemia, multiple myeloma, lymphoblastic leukemia, myelogenous leukemia, lymphocytic leukemia, myelocytic leukemia, Hodgkin's disease, non-Hodgkin's Lymphoma, Waldenstrom's macroglobulinemia, Heavy chain disease, and Polycythemia vera.

The present invention further provides kits to be used in assessing the expression of a particular RNA in a sample from a subject to assess the risk of developing disease. Kits include any combination of components that facilitates the performance of an assay. A kit that facilitates assessing the expression of an RNA may include suitable nucleic acid-based and immunological reagents as well as suitable buffers, control reagents, and printed protocols.

Kits that facilitate nucleic acid based methods may further include one or more of the following: specific nucleic acids such as oligonucleotides, labeling reagents, enzymes including PCR amplification reagents such as Taq or Pfu; reverse transcriptase, or one or more other polymerases, and/or reagents that facilitate hybridization. Specific nucleic acids may include nucleic acids, polynucleotides, oligonucleotides (DNA, or RNA), or any combination of molecules that includes one or more of the above, or any other molecular entity capable of specific binding to a nucleic acid marker. In one aspect of the invention, the specific nucleic acid comprises one or more oligonucleotides capable of hybridizing to the marker.

A specific nucleic acid may include a label. A label may be any substance capable of aiding a machine, detector, sensor, device, or enhanced or unenhanced human eye from differentiating a sample that that displays positive expression from a sample that displays reduced expression. Examples of labels include but are not limited to: a radioactive isotope or chelate thereof, a dye (fluorescent or nonfluorescent,) stain, enzyme, or nonradioactive metal. Specific examples include but are not limited to: fluorescein, biotin, digoxigenin, alkaline phosphatase, biotin, streptavidin, 3H, 14C, 32P, 35S, or any other compound capable of emitting radiation, rhodamine, 4-(4'-dimethylaminophenylazo) benzoic acid ("Dabcyl"); 4-(4'-dimethylaminophenylazo)sulfonic acid (sulfonyl chloride) ("Dabsyl"); 5-((2-aminoethyl)-amino)-naphtalene-1-sulfonic acid ("EDANS"); Psoralene derivatives, haptens, cyanines, acridines, fluorescent rhodol derivatives, cholesterol derivatives; ethylenediaminetetraaceticacid ("EDTA") and derivatives thereof or any other compound that signals the presence of the labeled nucleic acid. In one embodiment of the invention, the label includes one or more dyes optimized for use in genotyping. Examples of such dyes include but are not limited to: dR110, 5-FAM, 6FAM, dR6G, JOE, HEX, VIC, TET, dTAMRA, TAMRA, NED, dROX, PET, and LIZ.

An oligonucleotide is a reagent capable of binding a nucleic acid sequence. An oligonucleotide may be any polynucleotide of at least 2 nucleotides. Oligonucleotides may be less than 10, less than 15, less than 20, less than 30, less than 40, less than 50, less than 75, less than 100, less than 200, less than 500, or more than 500 nucleotides in length. While oligonucleotides are often linear, they may, depending on their sequence and conditions, assume a two- or three-dimensional structure. Oligonucleotides may be chemically synthesized by any of a number of methods including sequential synthesis, solid phase synthesis, or any other synthesis method now known or yet to be disclosed. Alternatively, oligonucleotides may be produced by recombinant DNA based methods. One skilled in the art would understand the length of oligonucleotide necessary to perform a particular task. Oligonucleotides may be directly labeled, used as primers in PCR or sequencing reactions, or bound directly to a solid substrate as in oligonucleotide arrays.

A nucleotide is an individual deoxyribonucleotide or ribonucleotide base. Examples of nucleotides include but are not limited to: adenine, thymine, guanine, cytosine, and uracil, which may be abbreviated as A, T, G, C, or U in representations of oligonucleotide or polynucleotide sequence. Any molecule of two or more nucleotide bases, whether DNA or RNA, may be termed a nucleic acid.

An oligonucleotide used to detect to an allele may be affixed to a solid substrate. Alternatively, the sample may be affixed to a solid substrate and the nucleic acid reagent placed into a mixture. For example, the nucleic acid reagent may be bound to a substrate in the case of an array or the sample may be bound to a substrate as the case of a Southern Blot, Northern blot or other method that affixes the sample to a substrate. A nucleic acid reagent or sample may be covalently bound to the substrate or it may be bound by some non covalent interaction including electrostatic, hydrophobic, hydrogen bonding, Van Der Waals, magnetic, or any other interaction by which an oligonucleotide may be attached to a substrate while maintaining its ability to recognize the allele to which it has specificity. A substrate may be any solid or semi solid material onto which a probe may be affixed, attached or printed, either singly or in the formation of a microarray. Examples of substrate materials include but are not limited to polyvinyl, polysterene, polypropylene, polyester or any other plastic, glass, silicon dioxide or other silanes, hydrogels, gold, platinum, microbeads, micelles and other lipid formations, nitrocellulose, or nylon membranes. The substrate may take any shape, including a spherical bead or flat surface.

A nucleotide is an individual deoxyribonucleotide or ribonucleotide base. Examples of nucleotides include but are not limited to: adenine, thymine, guanine, cytosine, and uracil, which may be abbreviated as A, T, G, C, or U in representations of oligonucleotide or polynucleotide sequence.

In some aspects of the invention, the probe may be affixed to a solid substrate. In other aspects of the invention, the sample may be affixed to a solid substrate. A probe or sample may be covalently bound to the substrate or it may be bound by some non covalent interaction including electrostatic, hydrophobic, hydrogen bonding, Van Der Waals, magnetic, or any other interaction by which a probe such as an oligonucleotide probe may be attached to a substrate while maintaining its ability to recognize the allele to which it has specificity. A substrate may be any solid or semi solid material onto which a probe may be affixed, attached or printed, either singly or in the formation of a microarray. Examples of substrate materials include but are not limited to polyvinyl, polysterene, polypropylene, polyester or any other plastic, glass, silicon dioxide or other silanes, hydrogels, gold, platinum, microbeads, micelles and other lipid formations, nitrocellulose, or nylon membranes. The substrate may take any form, including a spherical bead or flat surface. For example, the probe may be bound to a substrate in the case of an array. The sample may be bound to a substrate as (for example) the case of a Southern Blot, Northern blot or other method that affixes the sample to a substrate.

Kits may also contain reagents that detect proteins, often through the use of an antibody. These kits will contain one or more specific antibodies, buffers, and other reagents configured to detect binding of the antibody to the specific epitope. One or more of the antibodies may be labeled with a fluorescent, enzymatic, magnetic, metallic, chemical, or other label that signifies and/or locates the presence of specifically bound antibody. The kit may also contain one or more secondary antibodies that specifically recognize epitopes on other antibodies. These secondary antibodies may also be labeled. The concept of a secondary antibody also encompasses non-antibody ligands that specifically bind an epitope or label of another antibody. For example, streptavidin or avidin may bind to biotin conjugated to another antibody. Such a kit may also contain enzymatic substrates that change color or some other property in the presence of an enzyme that is conjugated to one or more antibodies included in the kit.

A kit may also contain an indication of a result of the use of the kit that signifies a particular physiological or cellular characteristic. An indication includes any guide to a result that would signal the presence or absence of any physiological or cellular state that the kit is configured to predict. For example, the indication may be expressed numerically, expressed as a color or density of a color, expressed as an intensity of a band, derived from a standard curve, or expressed in comparison to a control. The indication may be communicated through the use of a writing that may be contained physically in or on the kit (on a piece of paper for example), posted on the Internet, mailed to the user separately from the kit, or embedded in a software package. The writing may be in any medium that communicates how the result may be used to predict the cellular or physiological characteristic such as a printed document, a photograph, sound, color, or any combination thereof.

The invention further encompasses pharmaceutical compositions that include the disclosed compound as an ingredient. Such pharmaceutical compositions may take any physical form necessary depending on a number of factors including the desired method of administration and the physicochemical and stereochemical form taken by the disclosed compound or pharmaceutically acceptable salts of the compound. Such physical forms include a solid, liquid, gas, sol, gel, aerosol, or any other physical form now known or yet to be disclosed. The concept of a pharmaceutical composition including the disclosed compound also encompasses the disclosed compound or a pharmaceutically acceptable salt thereof without any other additive. The physical form of the invention may affect the route of administration and one skilled in the art would know to choose a route of administration that takes into consideration both the physical form of the compound and the disorder to be treated. Pharmaceutical compositions that include the disclosed compound may be prepared using methodology well known in the pharmaceutical art. A pharmaceutical composition that includes the disclosed compound may include a second effective compound of a distinct chemical formula from the disclosed compound. This second effective compound may have the same or a similar molecular target as the target or it may act upstream or downstream of the molecular target of the disclosed compound with regard to one or more biochemical pathways. Pharmaceutical compositions including the disclosed compound include materials capable of modifying the physical form of a dosage unit. In one nonlimiting example, the composition includes a material that forms a coating that holds in the compound. Materials that may be used in such a coating, include, for example, sugar, shellac, gelatin, or any other inert coating agent.

Pharmaceutical compositions including the disclosed compound may be prepared as a gas or aerosol. Aerosols encompass a variety of systems including colloids and pressurized packages. Delivery of a composition in this form may include propulsion of a pharmaceutical composition including the disclosed compound through use of liquefied gas or other compressed gas or by a suitable pump system. Aerosols may be delivered in single phase, bi-phasic, or tri-phasic systems.

In some aspects of the invention, the pharmaceutical composition including the disclosed compound is in the form of a solvate. Such solvates are produced by the dissolution of the disclosed compound in a pharmaceutically acceptable solvent. Pharmaceutically acceptable solvents include any mixtures of more than one solvent. Such solvents may include pyridine, chloroform, propan-1-ol, ethyl oleate, ethyl lactate, ethylene oxide, water, ethanol, and any other solvent that delivers a sufficient quantity of the disclosed compound to treat the affliction without serious complications arising from the use of the solvent in a majority of patients.

Pharmaceutical compositions that include the disclosed compound may also include a pharmaceutically acceptable carrier. Carriers include any substance that may be administered with the disclosed compound with the intended purpose of facilitating, assisting, or helping the administration or other delivery of the compound. Carriers include any liquid, solid, semisolid, gel, aerosol or anything else that may be combined with the disclosed compound to aid in its administration. Examples include diluents, adjuvants, excipients, water, oils (including petroleum, animal, vegetable or synthetic oils.) Such carriers include particulates such as a tablet or powder, liquids such as an oral syrup or injectable liquid, and inhalable aerosols. Further examples include saline, gum acacia, gelatin, starch paste, talc, keratin, colloidal silica, and urea. Such carriers may further include binders such as ethyl cellulose, carboxymethylcellulose, microcrystalline cellulose, or gelatin; excipients such as starch, lactose or dextrins; disintegrating agents such as alginic acid, sodium alginate, Primogel, and corn starch; lubricants such as magnesium stearate or Sterotex; glidants such as colloidal silicon dioxide; sweetening agents such as sucrose or saccharin, a flavoring agent such as peppermint, methyl salicylate or orange flavoring, or coloring agents. Further examples of carriers include polyethylene glycol, cyclodextrin, oils, or any other similar liquid carrier that may be formulated into a capsule. Still further examples of carriers include sterile diluents such as water for injection, saline solution, physiological saline, Ringer's solution, isotonic sodium chloride, fixed oils such as synthetic mono or digylcerides, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose, thickening agents, lubricating agents, and coloring agents.

The pharmaceutical composition including the disclosed compound may take any of a number of formulations depending on the physicochemical form of the composition and the type of administration. Such forms include solutions, suspensions, emulsions, tablets, pills, pellets, capsules, capsules including liquids, powders, sustained-release formulations, directed release formulations, lyophylates, suppositories, emulsions, aerosols, sprays, granules, powders, syrups, elixirs, or any other formulation now known or yet to be disclosed. Additional examples of suitable pharmaceutical carriers are described in "Remington's Pharmaceutical Sciences" by E. W. Martin, hereby incorporated by reference in its entirety.

Methods of administration include, but are not limited to, oral administration and parenteral administration. Parenteral administration includes, but is not limited to intradermal, intramuscular, intraperitoneal, intravenous, subcutaneous, intranasal, epidural, sublingual, intramsal, intracerebral, iratraventricular, intrathecal, intravaginal, transdermal, rectal, by inhalation, or topically to the ears, nose, eyes, or skin. Other methods of administration include but are not limited to infusion techniques including infusion or bolus injection, by absorption through epithelial or mucocutaneous linings such as oral mucosa, rectal and intestinal mucosa. Compositions for parenteral administration may be enclosed in ampoule, a disposable syringe or a multiple-dose vial made of glass, plastic or other material.

Administration may be systemic or local. Local administration is administration of the disclosed compound to the area in need of treatment. Examples include local infusion during surgery; topical application, by local injection; by a catheter; by a suppository; or by an implant. Administration may be by direct injection at the site (or former site) of a cancer, tumor, or precancerous tissue or into the central nervous system by any suitable route, including intraventricular and intrathecal injection. Intraventricular injection can be facilitated by an intraventricular catheter, for example, attached to a reservoir, such as an Ommaya reservoir. Pulmonary administration may be achieved by any of a number of methods known in the art. Examples include use of an inhaler or nebulizer, formulation with an aerosolizing agent, or via perfusion in a fluorocarbon or synthetic pulmonary surfactant. The disclosed compound may be delivered in the context of a vesicle such as a liposome or any other natural or synthetic vesicle.

A pharmaceutical composition formulated so as to be administered by injection may be prepared by dissolving the disclosed compound with water so as to form a solution. In addition, a surfactant may be added to facilitate the formation of a homogeneous solution or suspension. Surfactants include any complex capable of non-covalent interaction with the disclosed compound so as to facilitate dissolution or homogeneous suspension of the compound.

Pharmaceutical compositions including the disclosed compound may be prepared in a form that facilitates topical or transdermal administration. Such preparations may be in the form of a liquid solution, cream, paste, lotion, shake lotion, powder, emulsion, ointment, gel base, transdermal patch or iontophoresis device. Examples of bases used in such compositions include opetrolatum, lanolin, polyethylene glycols, beeswax, mineral oil, diluents such as water and alcohol, and emulsifiers and stabilizers, thickening agents, or any other suitable base now known or yet to be disclosed.

Addition of a pharmaceutical composition to cancer cells includes all actions by which an effect of the pharmaceutical composition on the cancer cell is realized. The type of addition chosen will depend upon whether the cancer cells are in vivo, ex vivo, or in vitro, the physical or chemical properties of the pharmaceutical composition, and the effect the composition is to have on the cancer cell. Nonlimiting examples of addition include addition of a solution including the pharmaceutical composition to tissue culture media in which in vitro cancer cells are growing; any method by which a pharmaceutical composition may be administered to an animal including intravenous, per os, parenteral, or any other of the methods of administration; or the activation or inhibition of cells that in turn have effects on the cancer cells such as immune cells (e.g. macophages and CD8+ T cells) or endothelial cells that may differentiate into blood vessel structures in the process of angiogenesis or vasculogenesis.

Determination of an effective amount of the disclosed compound is within the capability of those skilled in the art, especially in light of the detailed disclosure provided herein. The effective amount of a pharmaceutical composition used to effect a particular purpose as well as a pharmacologically acceptable dose determined by toxicity, excretion, and overall tolerance may be determined in cell cultures or experimental animals by pharmaceutical and toxicological procedures either known now by those skilled in the art or by any similar method yet to be disclosed. One example is the determination of the IC50 (half maximal inhibitory concentration) of the pharmaceutical composition in vitro in cell lines or target molecules. Another example is the determination of the LD50 (lethal dose causing death in 50% of the tested animals) of the pharmaceutical composition in experimental animals. The exact techniques used in determining an effective amount will depend on factors such as the type and physical/chemical properties of the pharmaceutical composition, the property being tested, and whether the test is to be performed in vitro or in vivo. The determination of an effective amount of a pharmaceutical composition will be well known to one of skill in the art who will use data obtained from any tests in making that determination. Determination of an effective amount of disclosed compound for addition to a cancer cell also includes the determination of an effective therapeutic amount, including the formulation of an effective dose range for use in vivo, including in humans.

Treatment is contemplated in living entities including but not limited to mammals (particularly humans) as well as other mammals of economic or social importance, including those of an endangered status. Further examples include livestock or other animals generally bred for human consumption and domesticated companion animals. The toxicity and therapeutic efficacy of a pharmaceutical composition may be determined by standard pharmaceutical procedures in cell cultures or animals. Examples include the determination of the IC50 (the half maximal inhibitory concentration) and the LD50 (lethal dose causing death in 50% of the tested animals) for a subject compound. The data obtained from these cell culture assays and animal studies can be used in formulating a range of dosage for use in human. The dosage may vary depending upon the dosage form employed and the route of administration utilized.

The effective amount of the disclosed compound to results in the slowing of expansion of the cancer cells would preferably result in a concentration at or near the target tissue that is effective in slowing cellular expansion in cancer cells, but have minimal effects on non-cancer cells, including non-cancer cells exposed to radiation or recognized chemotherapeutic chemical agents. Concentrations that produce these effects can be determined using, for example, apoptosis markers such as the apoptotic index and/or caspase activities either in vitro or in vivo.

Treatment of a condition is the practice of any method, process, or procedure with the intent of halting, inhibiting, slowing or reversing the progression of a disease, disorder or condition, substantially ameliorating clinical symptoms of a disease disorder or condition, or substantially preventing the appearance of clinical symptoms of a disease, disorder or condition, up to and including returning the diseased entity to its condition prior to the development of the disease.

The addition of a therapeutically effective amount of the disclosed compound encompasses any method of dosing of a compound. Dosing of the disclosed compound may include single or multiple administrations of any of a number of pharmaceutical compositions that include the disclosed compound as an active ingredient. Examples include a single administration of a slow release composition, a course of treatment involving several treatments on a regular or irregular basis, multiple administrations for a period of time until a diminution of the disease state is achieved, preventative treatments applied prior to the instigation of symptoms, or any other dosing regimen known in the art or yet to be disclosed that one skilled in the art would recognize as a potentially effective regimen. A final dosing regimen including the regularity of and mode of administration will be dependent on any of a number of factors including but not limited to the subject being treated; the severity of the affliction; the manner of administration, the stage of disease development, the presence of one or more other conditions such as pregnancy, infancy, or the presence of one or more additional diseases; or any other factor now known or yet to be disclosed that affects the choice of the mode of administration, the dose to be administered and the time period over which the dose is administered.

Pharmaceutical compositions that include the disclosed compound may be administered prior to, concurrently with, or after administration of a second pharmaceutical composition that may or may not include the compound. If the compositions are administered concurrently, they are administered within one minute of each other. If not administered concurrently, the second pharmaceutical composition may be administered a period of one or more minutes, hours, days, weeks, or months before or after the pharmaceutical composition that includes the compound Alternatively, a combination of pharmaceutical compositions may be cyclically administered. Cycling therapy involves the administration of one or more pharmaceutical compositions for a period of time, followed by the administration of one or more different pharmaceutical compositions for a period of time and repeating this sequential administration, in order to reduce the development of resistance to one or more of the compositions, to avoid or reduce the side effects of one or more of the compositions, and/or to improve the efficacy of the treatment.

The invention further encompasses kits that facilitate the administration of the disclosed compound to a diseased entity. An example of such a kit includes one or more unit dosages of the compound. The unit dosage would be enclosed in a preferably sterile container and would be comprised of the disclosed compound and a pharmaceutically acceptable carrier. In another aspect, the unit dosage would comprise one or more lyophilates of the compound. In this aspect of the invention, the kit may include another preferably sterile container enclosing a solution capable of dissolving the lyophilate. However, such a solution need not be included in the kit and may be obtained separately from the lyophilate. In another aspect, the kit may include one or more devices used in administrating the unit dosages or a pharmaceutical composition to be used in combination with the compound. Examples of such devices include, but are not limited to, a syringe, a drip bag, a patch or an enema. In some aspects of the invention, the device comprises the container that encloses the unit dosage.

Pharmaceutical compositions including the disclosed compound may be used in methods of treating cancer. Such methods involve the administration of a therapeutic amount of a pharmaceutical composition that includes the disclosed compound and/or a pharmaceutically acceptable salt thereof to a mammal, preferably a mammal in which a cancer has been diagnosed.

A therapeutic amount further includes the prevention of progression of the cancer to a neoplastic, malignant or metastatic state. Such preventative use is indicated in conditions known or suspected of preceding progression to cancer, in particular, where non- or precancerous cell growth consisting of hyperplasia, metaplasia, or most particularly, dysplasia has occurred (for review of such abnormal growth conditions, see Robbins and Angell, 1976, Basic Pathology, 2d Ed., W. B. Saunders Co., Philadelphia, pp. 68-90, incorporated by reference). Hyperplasia is a form of controlled cell proliferation involving an increase in cell number in a tissue or organ, without significant alteration in structure or activity. For example, endometrial hyperplasia often precedes endometrial cancer and precancerous colon polyps often transform into cancerous lesions. Metaplasia is a form of controlled cell growth in which one type of adult or fully differentiated cell substitutes for another type of adult cell. Metaplasia can occur in epithelial or connective tissue cells. A typical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

Alternatively or in addition to the presence of abnormal cell growth characterized as hyperplasia, metaplasia, or dysplasia, the presence of one or more characteristics of a transformed phenotype or of a malignant phenotype, displayed in vivo or displayed in vitro by a cell sample derived from a patient can indicate the desirability of prophylactic/therapeutic administration of the pharmaceutical composition that includes the compound. Such characteristics of a transformed phenotype include morphology changes, looser substratum attachment, loss of contact inhibition, loss of anchorage dependence, protease release, increased sugar transport, decreased serum requirement, expression of fetal antigens, disappearance of the 250,000 dalton cell surface protein, etc. Further examples include leukoplakia, featuring a benign-appearing hyperplastic or dysplastic lesion of the epithelium, or Bowen's disease, a carcinoma in situ. Both of theses are pre-cancerous lesions indicative of the desirability of prophylactic intervention. In another example, fibrocystic disease including cystic hyperplasia, mammary dysplasia, adenosis, or benign epithelial hyperplasia is indicates desirability of prophylactic intervention.

In some aspects of the invention, use of the disclosed compound may be determined by one or more physical factors such as tumor size and grade or one or more molecular markers and/or expression signatures that indicate prognosis and the likely response to treatment with the compound. For example, determination of estrogen (ER) and progesterone (PR) steroid hormone receptor status has become a routine procedure in assessment of breast cancer patients. See, for example, Fitzgibbons et al, Arch. Pathol. Lab. Med. 124:966-78, 2000, incorporated by reference. Tumors that are hormone receptor positive are more likely to respond to hormone therapy and also typically grow less aggressively, thereby resulting in a better prognosis for patients with ER+/PR+ tumors. In a further example, overexpression of human epidermal growth factor receptor 2 (HER-2/neu), a transmembrane tyrosine kinase receptor protein, has been correlated with poor breast cancer prognosis (see, e.g., Ross et al, The Oncologist 8:307-25, 2003), and Her-2 expression levels in breast tumors are used to predict response to the anti-Her-2 monoclonal antibody therapeutic trastuzumab (Herceptin®, Genentech, South San Francisco, Calif.).

In another aspect of the invention, the diseased entity exhibits one or more predisposing factors for malignancy that may be treated by administration of a pharmaceutical composition including the compound. Such predisposing factors include but are not limited to chromosomal translocations associated with a malignancy such as the Philadelphia chromosome for chronic myelogenous leukemia and t (14; 18) for follicular lymphoma; an incidence of polyposis or Gardner's syndrome that are indicative of colon cancer; benign monoclonal gammopathy which is indicative of multiple myeloma, kinship with persons who have had or currently have a cancer or precancerous disease, exposure to carcinogens, or any other predisposing factor that indicates in increased incidence of cancer now known or yet to be disclosed.

The invention further encompasses methods of treating cancer that comprise combination therapies that comprise the administration of a pharmaceutical composition including the disclosed compound and another treatment modality. Such treatment modalities include but are not limited to, radiotherapy, chemotherapy, surgery, immunotherapy, cancer vaccines, radioimmunotherapy, treatment with pharmaceutical compositions other than those which include the disclosed compound, or any other method that effectively treats cancer in combination with the disclosed compound now known or yet to be disclosed. Combination therapies may act synergistically. That is, the combination of the two therapies is more effective than either therapy administered alone. This results in a situation in which lower dosages of both treatment modality may be used effectively. This in turn reduces the toxicity and side effects, if any, associated with the administration either modality without a reduction in efficacy.

In another aspect of the invention, the pharmaceutical composition including the disclosed compound is administered in combination with a therapeutically effective amount of radiotherapy. The radiotherapy may be administered concurrently with, prior to, or following the administration of the pharmaceutical composition including the compound. The radiotherapy may act additively or synergistically with the pharmaceutical composition including the compound. This particular aspect of the invention would be most effective in cancers known to be responsive to radiotherapy. Cancers known to be responsive to radiotherapy include, but are not limited to, Non-Hodgkin's lymphoma, Hodgkin's disease, Ewing's sarcoma, testicular cancer, prostate cancer, ovarian cancer, bladder cancer, larynx cancer, cervical cancer, nasopharynx cancer, breast cancer, colon cancer, pancreatic cancer, head and neck cancer, esophogeal cancer, rectal cancer, small-cell lung cancer, non-small cell lung cancer, brain tumors, other CNS neoplasms, or any other such tumor now known or yet to be disclosed.

Examples of pharmaceutical compositions that may be used in combination with the disclosed compound may include nucleic acid binding compositions such as cis-diamminedichloro platinum (II) (cisplatin), doxorubicin, 5-fluorouracil, taxol, and topoisomerase inhibitors such as etoposide, teniposide, irinotecan and topotecan. Still other pharmaceutical compositions include antiemetic compositions such as metoclopromide, domperidone, prochlorperazine, promethazine, chlorpromazine, trimethobenzamide, ondansetron, granisetron, hydroxyzine, acethylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinols, thiethylperazine, thioproperazine and tropisetron.

Still other examples of pharmaceutical compositions that may be used in combination with the pharmaceutical composition including the disclosed compound are hematopoietic colony stimulating factors. Examples of hematopoietic colony stimulating factors include, but are not limited to, filgrastim, sargramostim, molgramostim and epoietin alfa. Alternatively, the pharmaceutical composition including the disclosed compound may be used in combination with an anxiolytic agent. Examples of anxiolytic agents include, but are not limited to, buspirone, and benzodiazepines such as diazepam, lorazepam, oxazapam, chlorazepate, clonazepam, chlordiazepoxide and alprazolam.

Pharmaceutical compositions that may be used in combination with pharmaceutical compositions that include the disclosed compound may include analgesic agents. Such agents may be opioid or non-opioid analgesic. Non-limiting examples of opioid analgesics inlcude morphine, heroin, hydromorphone, hydrocodone, oxymorphone, oxycodone, metopon, apomorphine, normorphine, etorphine, buprenorphine, meperidine, lopermide, anileridine, ethoheptazine, piminidine, betaprodine, diphenoxylate, fentanil, sufentanil, alfentanil, remifentanil, levorphanol, dextromethorphan, phenazocine, pentazocine, cyclazocine, methadone, isomethadone and propoxyphene. Suitable non-opioid analgesic agents include, but are not limited to, aspirin, celecoxib, rofecoxib, diclofinac, diflusinal, etodolac, fenoprofen, flurbiprofen, ibuprofen, ketoprofen, indomethacin, ketorolac, meclofenamate, mefanamic acid, nabumetone, naproxen, piroxicam, sulindac or any other analgesic now known or yet to be disclosed.

In other aspects of the invention, pharmaceutical compositions including the disclosed compound may be used in combination with a method that involves treatment of cancer ex vivo. One example of such a treatment is an autologous stem cell transplant. In this method, a diseased entity's autologous hematopoietic stem cells are harvested and purged of all cancer cells. A therapeutic amount of a pharmaceutical composition including the disclosed compound may then be administered to the patient prior to restoring the entity's bone marrow by addition of either the patient's own or donor stem cells.

Cancers that may be treated by pharmaceutical compositions including the disclosed compound either alone or in combination with another treatment modality include solid tumors such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma.

Additional cancers that may be treated by pharmaceutical compositions including the disclosed compound include blood borne cancers such as acute lymphoblastic leukemia ("ALL,"), acute lymphoblastic B-cell leukemia, acute lymphoblastic T-cell leukemia, acute myeloblastic leukemia ("AML"), acute promyelocytic leukemia ("APL"), acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia ("CML"), chronic lymphocytic leukemia ("CLL"), hairy cell leukemia, multiple myeloma, lymphoblastic leukemia, myelogenous leukemia, lymphocytic leukemia, myelocytic leukemia, Hodgkin's disease, non-Hodgkin's Lymphoma, Waldenstrom's macroglobulinemia, Heavy chain disease, and Polycythemia vera.

Examples that represent different aspects of the invention follow. Such examples should not be construed as limiting the scope of the disclosure. Alternative mechanistic pathways and analogous structures within the scope of the invention would be apparent to those skilled in the art.

The invention encompasses inhibitors of cell migration activity and inhibitors of effector recruitment activity. Inhibition encompasses any action that hinders, from any detectable level up to and including complete inactivation, the progression of a biological process. Such biological processes include expression of a gene or activities of a gene product, progression of a disease, normal and abnormal metabolic activities, interactions between entities within an organism, or interactions between one organism and another. Further nonlimiting examples of biological processes include development, death, maturation, infection, pain, apoptosis, or homeostasis. Inhibition includes actions that silence or repress the expression of a gene. Inhibition also includes actions that hinder the activity of the RNA product, protein product, or postranslationally modified protein product of a gene. Inhibition may be effectuated through a single agent that inactivates a single gene or gene product, by a single agent that inactivates a combination of more than one gene or gene product, a combination of agents that inactivates a single gene or gene product or a combination of agents that inactivates a combination of more than one gene or gene product.

Inhibition may be effectuated directly by an agent that directly causes the inhibition of a biological process or by agents that trigger one or more different biological processes to effectuate the inhibition of the first biological process. Agents that cause inhibition may also be called inhibitors. Examples of inhibitors include compositions such as compounds that trigger RNAi silencing such as microRNA or siRNA, small molecular compounds, proteins such as soluble receptors or antibodies or any fragment thereof, including an Fab, $F(ab)_2$, Fv, scFv, Fc, phage display antibody, peptibody or any other composition of matter that may inactivate or hinder a biological process. Further nonlimiting examples of inhibitors include X-rays, UV rays, visible light including laser light, and sound.

Cell migration activity includes any mode through which a cell may move in two-dimensional or three-dimensional space. Such migration includes movement through the use of pseudopodia including the adhesion of pseudopodia to a surface, a flagellum, a cilium, acts of amoeboid movement, extravasation, myosin-actin interactions, microtubule extension, or any other process through which a cell moves itself from one place to another or changes its morphology. In one aspect of the invention, cell migration activity is measured through cell adhesion. Using adhesion, cell migration activity may be measured by cell-cell aggregation, monolayer radial migration, including adhesion to a cell matrix comprising laminin, BSA or any other cell matrix component, three dimensional spheroid dispersion, or any other method that measures adhesion based cellular migration in space. Migration activity may be measured by any method that detects that a cell has moved from one place to another or has changed its morphology. Such methods include flow cytometry, capillary electrophoresis, visual examination by light, fluorescence, or electron microscopy, or any such method known in the art or yet to be developed. Inhibitors of cell migration activity are agents that disrupt any molecular or cellular process involved in cell migration activity.

Effector recruitment activity includes any activity of a protein that contributes to the formation of a complex of two or more molecules that serves to catalyze one or more chemical reactions. Effectors include any protein, nucleic acid or other molecule that may be included in a complex that performs one or more biological activities. Recruitment activity encompasses any protein-protein interaction including phosphorylation, dephosphorylation and other enzymatic activities, adhesion, signaling cascades, and cytokine/chemokine interactions, any protein-nucleic acid interactions, such as any of those involved in transcription, translation or DNA replication, or any other process that includes a protein interacting with another molecule. Inhibitors of effector recruitment activity may disrupt the interaction of a molecule with any of the proteins listed above, the interaction between any of those proteins with each other, and further includes any members of a complex that might be later identified.

In one aspect of the invention, inhibitors of effector recruitment activity may be identified on the basis of their ability to disrupt the binding of a molecule to one or more of its effectors. This specific binding may be measured by any method that allows the measurement of a protein-protein interaction known in the art. Such method include the following examples, alone or in combination as necessary: co-immunoprecipitation, biomolecular fluorescence complementation, fluorescence resonance energy transfer, label transfer, a yeast two-hybrid screen, in-vivo crosslinking, tandem affinity purification, chemical crosslinking, quantitative immunoprecipitation combined with knock-down (QUICK), dual polarization interferometry, protein-protein docking, static light scattering, immunoprecipitation plus mass-spectrometry, Strep-protein interaction experiment (SPINE), surface plasmon resonance, fluorescence correlation spectroscopy, or any other method of measuring the specific interaction between one protein and another now known in the art or yet to be disclosed.

In another aspect of the invention a glioblastoma patient is treated by first assessing the expression of a target and then treating with an effective dose of an inhibitor of that target, potentially in combination with Temozolimide. The effective dose of a compound is that amount effective to prevent occurrence of the symptoms of a disorder or to treat some symptoms of the disorder from which the patient suffers. Effective dose also includes an effective amount, a therapeutic amount, or any amount sufficient to elicit the desired pharmacological or therapeutic effects, thus resulting in effective prevention or treatment of the disorder. Thus, when treating a patient with glioblastoma, an effective amount of compound is an amount sufficient to slow, or arrest the progression, migration, metastasis, growth, or development of the tumor with the result that life is extended. Prevention includes a delay in onset of symptoms. Treatment includes a decrease in the symptoms associated with the disorder or an amelioration of the recurrence of the symptoms of the disorder. A pharmacologically acceptable dose encompasses any dose that may be administered to a patient that will not be lethal to the patient or cause effects that threaten the health or the life of the patient.

Patients include any human being, nonhuman primate, companion animal, or mammal suffering from a disease. In one aspect of the invention, the patient has symptoms that signify the presence of a tumor or other growth in the brain. Such symptoms include headache, seizures, mental or personality changes, mass effect, or one of a number of focal or localized systems including ringing or buzzing sounds, hearing loss, loss of coordination, reduced sensation, weakness or paralysis, difficulty with walking or speech, difficulty keeping balance, decreased muscle control, or double vision. Patients may display one or more different brain tumor types including acoustic neurinoma, astrocytoma, ependyoma, glioblastoma multiforme, meningioma, metastatic tumors originating from another tumor type, mixed glioblastoma, oligodendroglioblastoma, or pineal region tumor.

EXAMPLE

Elements and acts in the example are intended to illustrate the invention for the sake of simplicity and have not necessarily been rendered according to any particular sequence or embodiment. The example is also intended to establish possession of the invention by the Inventors.

The tumor necrosis factor (TNF) ligand superfamily and their cognate receptors are involved in the regulation of various cellular responses including proliferation, differentiation, and apoptosis (See Reference 6). Of interest, TWEAK and its receptor Fn14 are members of the TNF and TNFR superfamilies, respectively, and TWEAK-Fn14 axis signaling has been implicated in cancer progression and survival (See Reference 7). It has been reported that Fn14 mRNA expression is up-regulated in migration-stimulated glioma cells in vitro and invading cells in vivo (See References 8 and 9). Across tumor grades, Fn14 is most significantly overexpressed in GBM tissue, whereas in normal brain tissue the expression of Fn14 is minimal-to-absent (See References 8 and 9). TWEAK binding to the Fn14 receptor activates the NF-κB signaling pathway (See References 10 and 11). Additionally, two key NF-κB-inducible proteins, Bcl-xL and Bcl-w, contribute to TWEAK-enhanced glioma cell resistance to cytotoxic-therapy induced apoptosis (See Reference 11). Bcl-xL cellular levels may be regulated through activation of the serine/threonine kinase Akt/protein kinase B, a downstream effector of the PI3K pathway (See Reference 12). To date, three members of this family, Akt1, Akt2, and Akt3, have been identified and are independently activated by phosphorylation on conserved serine residues at aa473 10 (Akt1), aa474 (Akt2), or aa472 (Akt3), as well as on threonine residues at aa308 (Akt1), aa309 (Akt2) or aa305 (Akt3) (See Reference 13). The isoforms share many common substrates through their preferential phosphorylation of a motif with the sequence RxRXX(S/T) (See Reference 14). Several Akt-regulated gene products have been identified that have roles in the regulation of apoptosis, including the proapoptotic proteins BAD and caspase-9 (See References 15 and 16). Activated Akt increases Bcl-xL protein stability through the phosphorylation of BAD on Ser-136 (See Reference 15). Phosphorylated BAD is sequestered in the cytoplasm by interacting with 14-3-3 scaffolding proteins, thus blocking BAD binding to Bcl-xL (See Reference 15).

Although the three Akt isoforms are structurally homologous and share similar mechanisms of activation, they exhibit distinct biological features. For instance, Akt1 is more highly expressed in tissues such as the thymus and lung, whereas Akt2 overexpression has been found in cancer of the ovary, breast and pancreas where it has been implicated in the processes of invasion and metastasis (See References 17-23). In contrast, Akt3 has been reported to be more limited in tissue distribution, with high levels in brain, heart and kidney (See Reference 24) and appears to promote melanoma cell survival (See Reference 25.) TWEAK is a survival factor for glioma cells. This effect depends on the activation of the NF-κB pathway and subsequent up-regulation of Bcl-xL and Bcl-w protein expression (See Reference 11). Further, TWEAK stimulation results in Akt activation and phosphorylaton of the pro-apoptotic protein BAD. Activation of Fn14 by TWEAK results in phosphorylation of both Akt1 and Akt2. However, siRNA-mediated depletion of Akt1 or Akt2 showed that BAD serine 136 phosphorylation is dependent specifically on Akt2 activity. Inhibition of Akt2 expression by siRNA also abrogates TWEAK-induced glioma cell survival, whereas no effect on glioma cell survival was observed after siRNA-mediated inhibition of Akt1 expression. Furthermore, Akt2 mRNA expression levels positively correlate with both brain tumor grade and malignancy, and with poor clinical outcome. Finally, Akt2 protein levels correlate with Fn14 protein levels in GBM specimens, supporting the notion that Fn14 signaling through Akt2 may contribute to the poor response observed when patients with brain tumors are treated with chemo- and radiationtherapy.

Materials and Methods

Cell culture conditions. Human astrocytoma cell lines T98G, U87, U118, SNB19 (American Type Culture Collection) and SF767 (University of California at San Francisco) were maintained in Dulbecco's modified Eagle's medium (DMEM)+10% heat inactivated fetal bovine serum (FBS) in a 37° C., 5% $CO_2$ atmosphere. In all assays treated with TWEAK, cells were cultured in reduced serum (0.5% FBS) for 16 h prior to stimulation with recombinant TWEAK at 100 ng/ml in DMEM+0.1% BSA for the indicated times.

Western blot and immunoprecipitation assays. Immunoblotting and protein determination experiments were performed as described previously (See Reference 11). In some experiments, TWEAK (100 ng/ml) was preincubated with 2.5 µg/ml soluble Fn14-Fc decoy receptor or control Fc protein at 37° C. for 15 min before adding it to cells (See Reference 26). Also, in some cases, cells were pretreated with the PI3K inhibitor LY294002 (10 µM) for 10 min prior to TWEAK addition. For immunoprecipitation, cells were lysed on ice for 10 min in a buffer containing 10 mM Tris-HCl, pH 7.4, 0.5% Nonidet P-40, 150 mM NaCl, 1 mM phenylmethylsulfonyl fluoride, 1 mM EDTA, 2 mM sodium vanadate, 10 µg/ml aprotinin, and 10 µg/ml leupeptin (Sigma). Equivalent amounts of protein (500 µg) were precleared and immunoprecipitated from the lysates, and then washed with lysis buffer followed by 51 buffer (10 mM HEPES, pH 7.4, 0.15 M NaCl, 2 mM EDTA, 1.5% Triton X-100, 0.5% deoxycholate, 0.2% SDS) (40). Samples were then resuspended in 2×SDS sample buffer and boiled in the presence of 2-mercaptoethanol (Sigma), separated by SDS-PAGE, transferred to nitrocellulose for 1 h at 4° C., and proteins were detected as described previously (See Reference 27). Small-interfering RNA preparation and transfection. Small interfering RNA (siRNA) oligonucleotides specific for Rac1 and GL2 Luciferase were previously described (See Reference 28). Transient transfection of siRNA was carried out as previously described (See Reference 28). All Akt-directed and Bad-directed siRNA were used at 25 nM, and no cell toxicity was observed. Maximum inhibition of protein levels was achieved 72 h after transfection.

PhosphoBAD (Ser 136) sandwich enzyme-linked immunosorbant Assay (ELISA). Phosphorylation levels of BAD (Ser 136) were determined using a cell-based ELISA. Glioma cells were transfected with siRNA oligonucleotides against AKT1, AKT2, or non-mammalian GL2 luciferase control siRNA and incubated overnight. The cells were cultured overnight in DMEM with 0.5% FBS prior to TWEAK or control PBS addition in DMEM with 0.1% BSA for 15 min. Total cellular lysates were collected according to manufacturer's instructions utilizing the PathScan Sandwich ELISA kit (Cell Signaling). Each sample (100 µg total protein) was diluted 1:1 in sample buffer for a final volume of 200 µL prior to addition to the designated microstrip wells previously coated by the manufacturer with a BAD rabbit monoclonal capture antibody. The microstrips were then sealed and incubated overnight at 4° C. on a plate shaker. Following extensive washing (4× with wash buffer), a phosphoBAD (Ser 136) antibody (diluted 1:1000) and total BAD antibody (diluted 1:1000) were added to their designated wells and incubated for 1 h at 37° C. The wells were then washed 4× with wash buffer prior to addition of the HRP-linked secondary antibody. Samples were incubated at 37° C. for 30 min, washed, and incubated with TMB substrate for 10 min. Stop solution was omitted and absorbance read at 600 nm (See Reference 29).

Apoptotic assay. Apoptotic cells were evaluated by nuclear morphology of DAPI stained cells as described previously (See Reference 11). Briefly, cells with condensed, fragmented chromatin were manually scored as apoptotic cells. At least five fields (total of 1000 cells) were evaluated, and data reported as apoptotic cells/total cells×100. Verification of apoptotic cells was conducted by co-immunofluorescence staining using a monoclonal antibody against activated cleaved caspase 3. At least 1000 cells per treatment were evaluated for condensed chromatin and activated caspase 3 (See Reference 11).

Expression profile dataset of AKT isoforms in human gliomas and normeoplastic brain. An expression microarray database consisting of 135 clinically annotated brain tumor specimens publicly available at NCBI's Gene Expression Omnibus as dataset GDS 1962 was used to explore expression of Akt isoforms. Snap-frozen specimens from epileptogenic foci (NB, n=24) and tumors [29 low-grade astrocytomas (LGAs) and 82 glioblastoma multiformes (GBMs)] with clinical information were collected at the Hermelin Brain Tumor Center, Henry Ford Hospital (Detroit, Mich.) as previously described (See Reference 9) Gene expression profiling as described previously (See Reference 9) was conducted on all samples using Affymetrix U133 Plus 2 GeneChips according to the manufacturer's protocol at the Neuro-Oncology Branch at the National Cancer Institute (Bethesda, Md.). Gene expression data were normalized in two ways: per chip normalization and per gene normalization across all samples in the collection. For per chip normalization, all expression data on a chip were normalized to the 50th percentile of all values on that chip. For per gene normalization, the data for a given gene were normalized to the median expression level of that gene across all samples. Gene expression differences were deemed statistically significant using parametric tests where variances were not assumed equal (Welch analysis of variance). Expression values were then filtered for highly variable (differentially expressed) genes (coefficient of variation >30%) across samples producing a list of 7322 genes. Principal component (PC) analysis was done to discern possible relationships between subgroups of samples as previously described (See Reference 9), and Kaplan-Meier survival curves were developed for each PC cluster. One cluster had a median survival time of 401 days (short-term survival, ST) and the other cluster had a median survival time of 952 days (long-term survival, LT). Box-and-whisker plots for AKT1, AKT2, and AKT3 expression levels in each cluster derived from PC analysis were graphed. Significance between the two populations was tested with a two-sample t-test assuming unequal variances.

Glioblastoma tissue microarray (TMA) and immunohistochemistry. Sections were obtained from a glioma invasion TMA master block containing representative punches of tumor core, edge, and invasive rim from 44 clinically-annotated cases of WHO grade-IV GBM specimens (according to standardized criteria from ten contributing institutes) as previously described (See Reference 30). The GBM samples were obtained from patients who underwent primary therapeutic subtotal or total tumor resection performed under image guidance. Specifically, each specimen block chosen for the TMA met the criteria of non-necrotic, nonirradiated or chemo-treated glioma tissue. Two separate face-cuts were made for each of the specimens used to construct the TMA. H&E staining was performed on the face-cuts to assist in the identification of the tumor cells. The face-cuts were reviewed by two independent experienced neuropathologists (Dr. Ken Aldape, MD Anderson and Dr. David Zagzag, New York University) who designated the areas of core (center of the tumor), edge (interface between tumor core and normal tissue front) and rim (region distal to the edge but still containing notable tumor cells). The TMA was constructed from representative punches of tumor core and invasive rim using an indexed manual arrayer with attached stereomicroscope under the direction of Dr. Galen Hostetter, who also reviewed and verified that the prescribed areas made by the neuropathologists were in agreement before punches were taken for the TMA paraffin block. Every 50th section from the TMA was stained with H&E to confirm tissue morphology and invasive feature of the GBM cells. IHC analysis for Fn14 was done using an Fn14 monoclonal antibody, P4A8 (Biogen Idec, Inc., Cambridge, Mass.) as previously described (See Reference 9). Akt1 and Akt2 IHC analysis was performed using anti-Akt1 and anti-Akt2 antibodies, respectively. A scoring system for chromophore was used to capture the outcome: 0, negative; 1, weak; 2, moderate; 3-4, strong staining.

Statistical analysis. Statistical analyses were performed using the two-sample t-test and $\chi^2$-test. Tests for correlation using Pearson's correlation coefficient were calculated using the cor.test function in the R statistical package. $P<0.05$ was considered significant.

Results

TWEAK stimulates Akt-Ser473 phosphorylation through activation of the Fn14 receptor. TWEAK-stimulated glioma cells increase expression of the anti-apoptotic protein BclxL, resulting in an enhancement of glioma cell survival (See Reference 11). The protein kinase Akt is a critical regulator of cell survival and it has been reported that Akt activation can increase Bcl-xL protein stability (See References 27 and 31) however, it had yet to be determined whether or not TWEAK stimulation of glioma cells could affect the activation state of Akt. This was done by assessing the phosphorylation of Akt on serine-473. A serine-473 phospho-specific antibody capable of detecting the phosphorylation status of all Akt isoforms [at either serine 473 (Akt1), serine 474 (Akt2), or serine 472 (Akt3)] was used. Immunoblot analysis of whole cellular lysates of glioma cells after TWEAK treatment showed an induction of Akt-Ser473 phosphorylation (See FIG. 1). Phosphorylation of Akt-Ser473 was detected after 5 min for both T98G and SF767 cell lines upon TWEAK treatment. This phosphorylation diminished after more than 1 hour of TWEAK treatment. A soluble Fn14-Fc decoy receptor was added to the TWEAK prior to adding it to the cells in order to test whether TWEAK stimulation of Akt-Ser473 phosphorylation could be blocked with a TWEAK antagonist (See References 11 and 26). When the TWEAK was pretreated with Fn14-Fc decoy receptor prior to adding TWEAK to the cells, there was no increase in Akt-Ser473 phosphorylation. Pretreatment with a control decoy receptor (Fc only) still showed Akt-Ser473 (See FIG. 2). These results show that TWEAK binding to the Fn14 receptor induces Akt-Ser 473 phosphorylation. Two additional experiments were conducted to further investigate TWEAK activation of Akt phosphorylation. Glioma cells were treated with the PI3K inhibitor, LY294002. Because Akt-Ser473 phosphorylation was blocked in the presence of LY294002, TWEAK activation of Akt is dependent on PI3K (See FIG. 2). TWEAK has been reported to induce Rac1 activation (See Reference 9) and the PI3K-Akt pathway has been shown to be affected by Rac1 activity (See References 32-34.) However, it had yet to be shown that TWEAK is capable of inducing Akt-Ser473 phosphorylation through Rac1. Cells were transfected with siRNA configured to suppress Rac1 expression. The siRNA transfection resulted in a >90% suppression of Rac1 protein expression and abrogated TWEAK-induced Akt-Ser473 phosphorylation (See FIG. 3).

Figure 5:
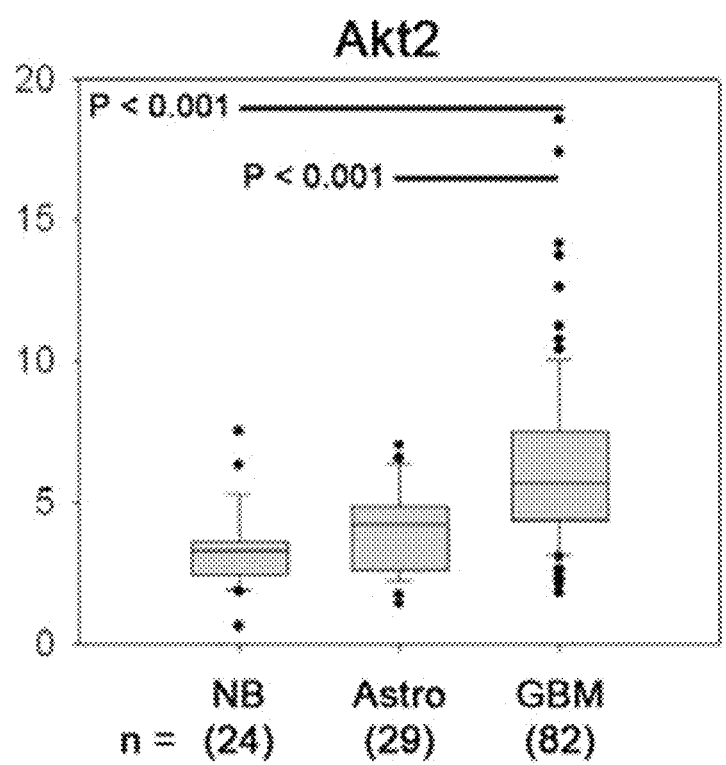
FIG. 5 depicts mRNA expression of Akt2 in brain tissue of the indicated type.
Figure 6:
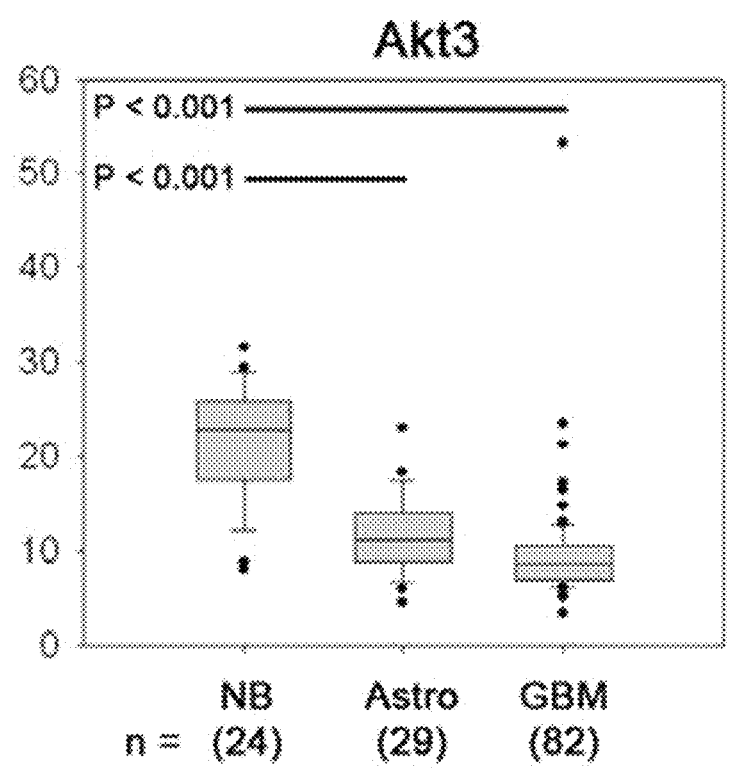
FIG. 6 depicts mRNA expression of Akt3 in brain tissue of the indicated type.

Analysis of Akt isoform expression profiling. Specific signaling roles for individual Akt isoforms have begun to emerge (See References 19, 35, 36.) Probes capable of hybridizing to each of the three Akt isoforms were used to survey global expression arrays from a panel of 24 non-neoplastic and 111 anaplastic astrocytoma and glioblastoma multiforme specimens (NCBI Gene Expression Omnibus dataset GSE4290). Both Akt1 and Akt2 mRNA expression levels correlated with increased glial tumor grade with highest expression in GBM specimens ($p<0.001$; FIG. 5). In contrast, Akt3 mRNA expression is relatively high in non-neoplastic brain specimens and appears to decrease in glial tumors, with low expression in GBM specimens ($p<0.001$; FIG. 6). Principle component analysis (PCA) was used to query the relationship between the expression of each of the Akt isoforms and patient outcome (See Reference 9). By PCA, GBM patients segregated into two separate clusters displaying distinct Kaplan-Meier survival curves. Cluster 1 has a median survival time of 952 days (long term, LT), whereas cluster 2 has a median survival of 401 days (short term, ST) (See Reference 9). Analysis of the expression value for each Akt isoform showed that GBM patients in the ST survival cluster had higher Akt1 ($p<0.01$) and Akt2 ($p<0.001$) mRNA levels than GBM patients in the LT survival cluster. In contrast, Akt3 mRNA expression is significantly higher in GBM patients in the LT survival cluster as compared to GBM patients in the ST survival cluster. These findings suggest that high Akt1 and Akt2 expression levels correlates with brain tumor grade and poor patient outcome.

Figure 11:
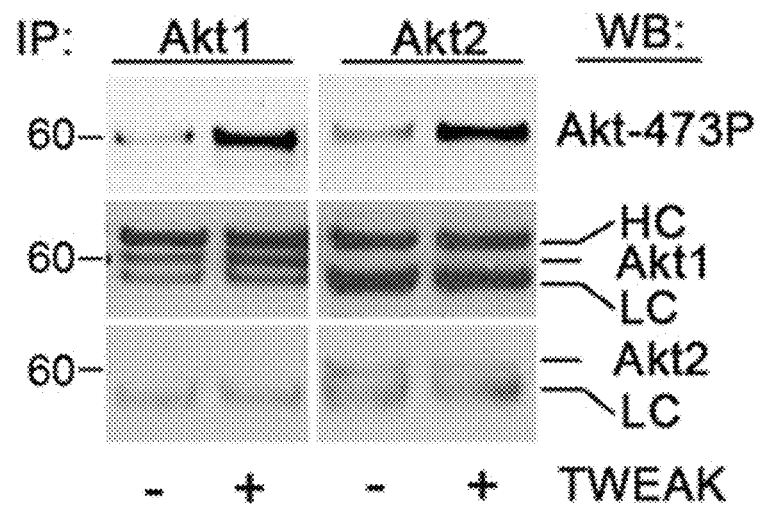
FIG. 11 depicts a western blot showing Akt1 and Akt2 phosphorylation in the presence or absence of TWEAK treatment.

Akt1 and Akt2 are co-expressed in glioma cell lines and phosphorylated upon TWEAK stimulation. The protein expression of Akt1 and Akt2 across five different glioma cell lines was assessed. Both Akt isoforms were present in all glioma cell lines (FIG. 11). Individual isoforms of Akt were immunoprecipitated the using isoform-specific antibodies, and then an immunoblot analysis was performed using a phospho-specific antibody to Akt-Ser473, which recognizes phospho-serine 473 on Akt1 and phospho-serine 474 on Akt2. A two-fold induction of phosphorylation of both Akt1 and Akt2 in T98G cells following TWEAK treatment was observed (See FIG. 11). Similar results were observed in SF767 cells. These findings indicate that TWEAK stimulation can result in both Akt1 and Akt2 activation.

Figure 12:
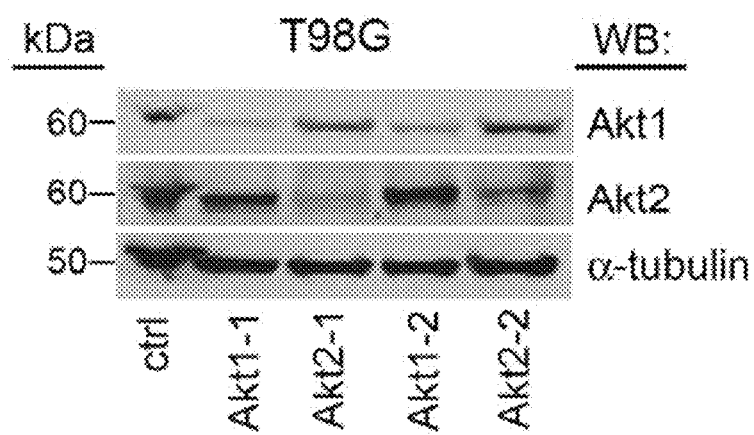
FIG. 12 depicts a western blot showing suppression of Akt1 and Atk2 expression by Akt1 and Akt2 siRNA in T98G cells.
Figure 13:
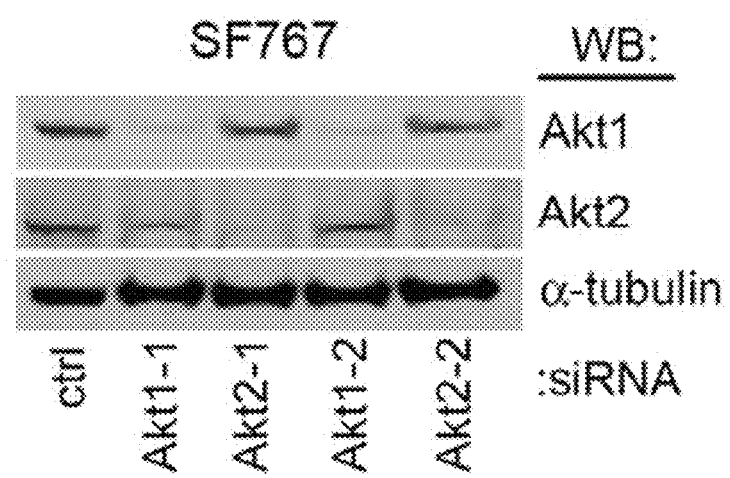
FIG. 13 depicts a western blot showing suppression of Akt1 and Akt2 expression by Akt1 and Akt2 siRNA in SF767 cells.
Figure 14:
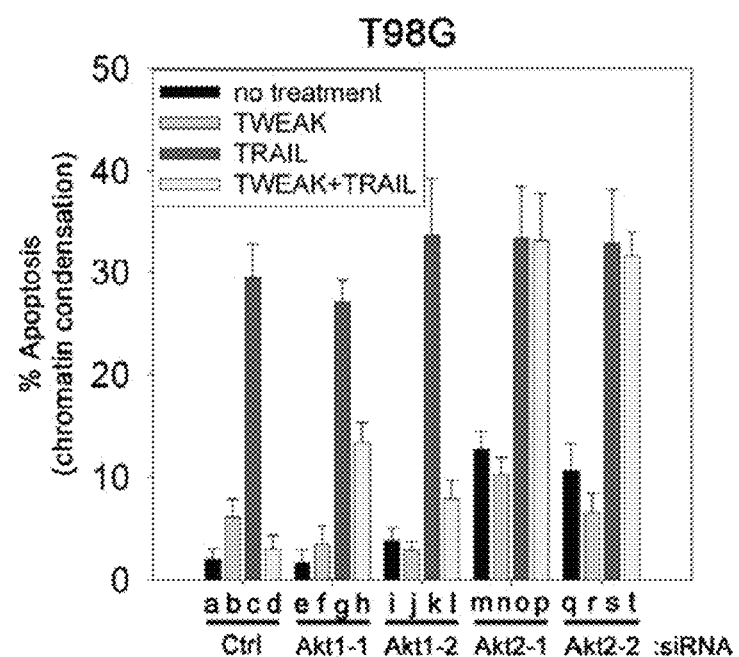
FIG. 14 depicts the percentage of apoptosis in T98G cells treated with TWEAK, TRAIL or TWEAK and TRAIL when Akt1 or Akt2 expression is suppressed.
Figure 15:
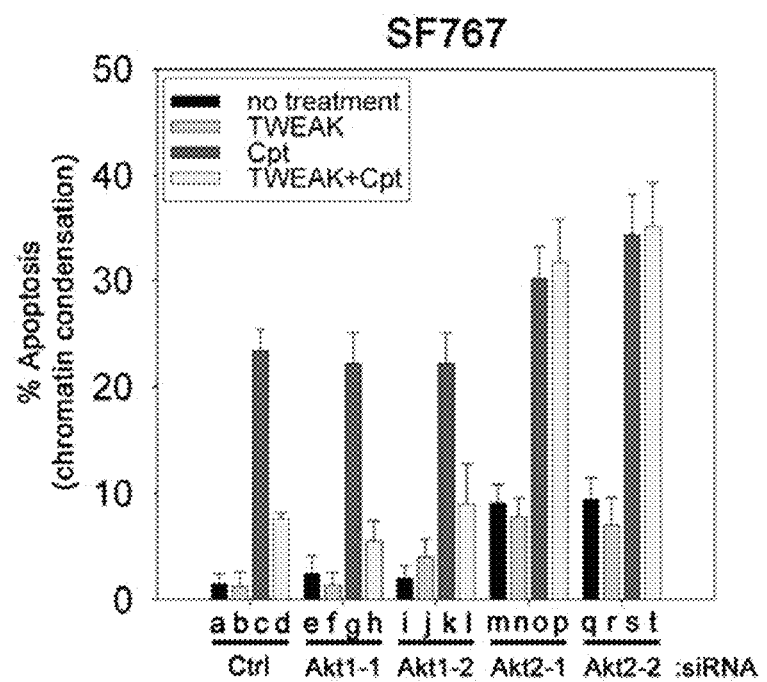
FIG. 15 depicts the percentage of apoptosis in SF767 cells treated with TWEAK, TRAIL or TWEAK and TRAIL when Akt1 or Akt2 expression is suppressed.
Figure 16:
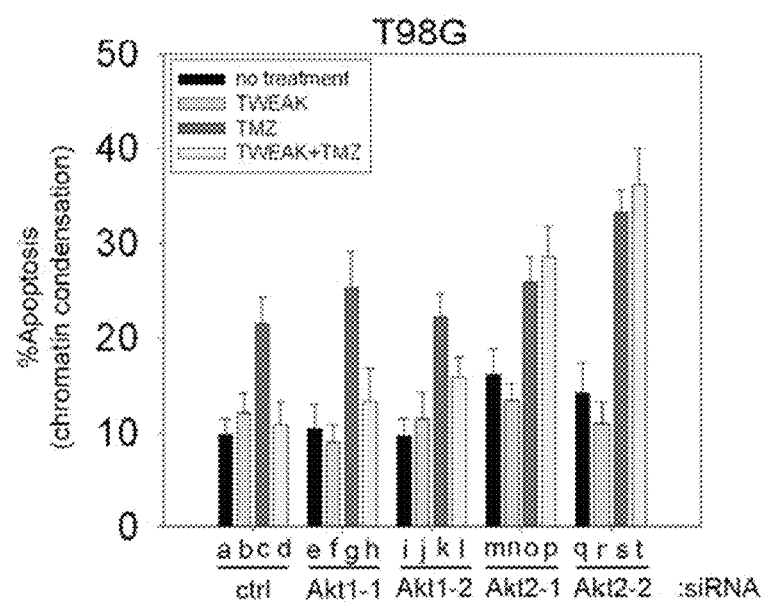
FIG. 16 depicts the percentage of apoptosis in T98G cells treated with TWEAK, TMZ, or TWEAK and TMZ when Akt1 or Akt2 expression is suppressed.
Figure 17:
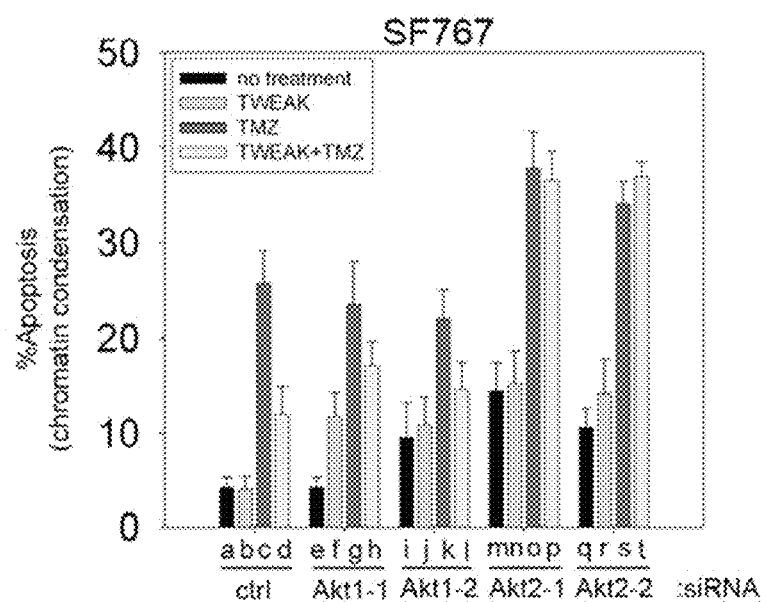
FIG. 17 depicts the percentage of apoptosis in SF767 cells treated with TWEAK, TMZ, or TWEAK and TMZ when Akt1 or Akt2 expression is suppressed.

TWEAK-induced glioma cell survival is dependent upon the Akt2 isoform. It has been reported that TWEAK stimulation of glioma cells results in diminished cytotoxic therapy induced apoptosis (See Reference 11). However, the role of Akt or any Akt isoforms is unknown. Expression of Akt1 and Akt2 was suppressed by transient transfection with small interfering RNA duplexes. Transfection was followed by treatment with the cytotoxic agents TRAIL or camptothecin. Two independent siRNA oligonucleotides were used to marker Akt1 and Akt2. Specificity of each siRNA for each isoform was confirmed and the level of suppression reached 80-90% (See FIGS. 12 and 13). While suppression of Akt1 expression has a minimal effect on glioma cell survival, increased apoptosis was detected in cells when Akt2 expression was suppressed relative to transfection with a control siRNA. Treatment of glioma cells transfected with control siRNA and treated with cytotoxic agents showed apoptosis. However, pretreatment of cells with TWEAK prior to the addition of the cytotoxic agents abrogated cytotoxic therapy-induced apoptosis. Suppression of Akt1 expression did not abrogate the TWEAK protective effect, but suppression of Akt2 expression resulted in a loss of TWEAK induced cell survival in the presence of the cytotoxic agents. These findings indicated that TWEAK-induced glioma cell survival is dependent upon Akt2 function. (FIGS. 14 and 15). Cellular apoptosis was detected in glioma cells treated with temozolimide (TMZ). However, pretreatment of the cells with TWEAK prior to TMZ addition suppressed TMZ induced cell death. Suppression of Akt2 expression with siRNA negated the TWEAK survival effect, while no effect on TWEAK survival was detected upon Akt1 depletion. These results show that TWEAK-Fn14 signaling through Akt2 can suppress chemotherapy-induced cell death in glioma.

Figure 18:
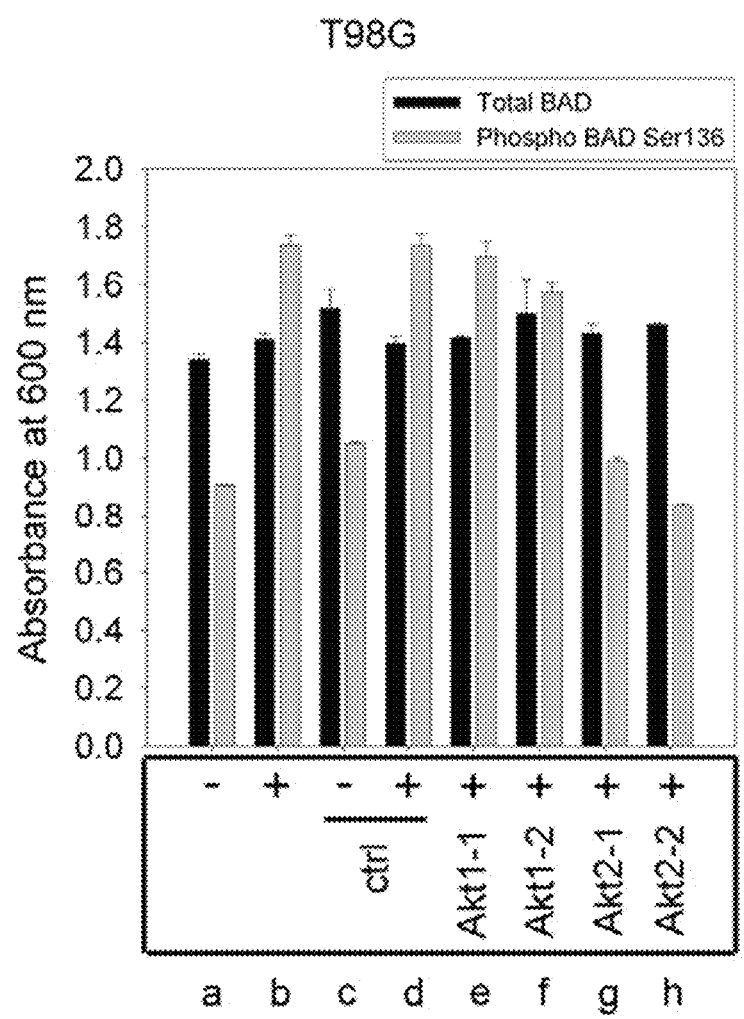
FIG. 18 depicts phosphorylation of BAD in T98G cells when Akt1 or Akt2 expression is suppressed.

TWEAK stimulation of BAD serine-136 phosphorylation is dependent upon Akt2 activity. It has been reported that one mechanism by which Akt activation increases cell survival is through the phosphorylation of the pro-apoptotic protein BAD on Ser136 (See Reference 12). However, it has not been reported whether or not TWEAK stimulation acts upon this pathway or whether or not different Akt isoforms have different effects. The phosphorylation state of BAD on Ser 136 was monitored using a cell-based ELISA. Upon TWEAK stimulation the amount of phosphorylated BAD-Ser136 increased approximately two-fold whereas the amount of total BAD did not change significantly. The expression of Akt1 or Akt2 was suppressed by transient transfection with siRNA. Suppression of Akt2 expression reduced TWEAK-induced BAD-Ser136 phosphorylation whereas suppression of Akt1 expression had no effect on BAD Ser-136 phosphorylation (FIG. 18).

Figure 20:
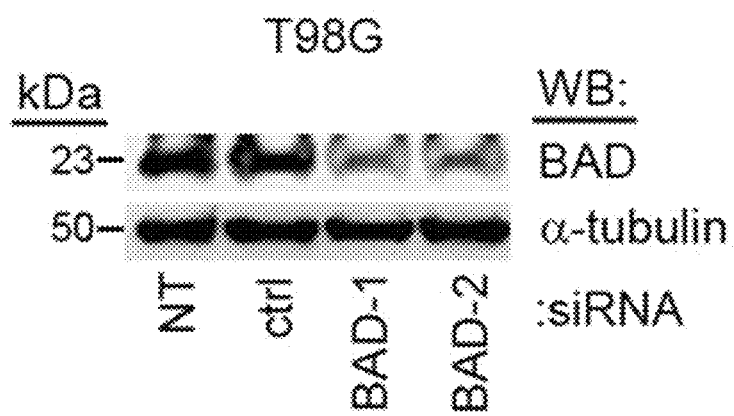
FIG. 20 depicts a western blot showing suppression of BAD expression in T98G cells in the presence of siRNA specific for BAD.
Figure 21:
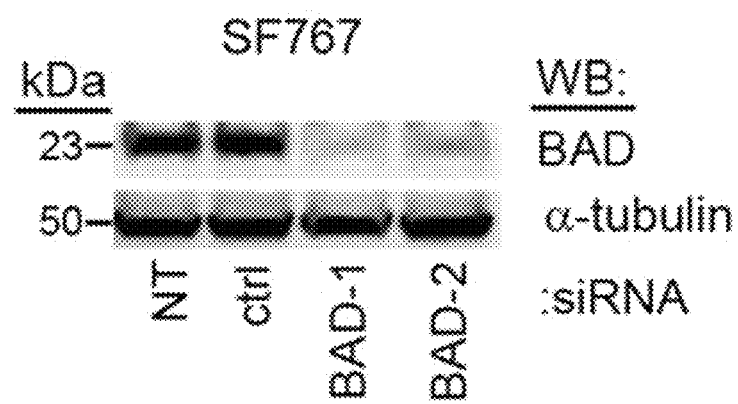
FIG. 21 depicts a western blot showing suppression of BAD expression in SF767 cells in the presence of siRNA specific for BAD.
Figure 22:
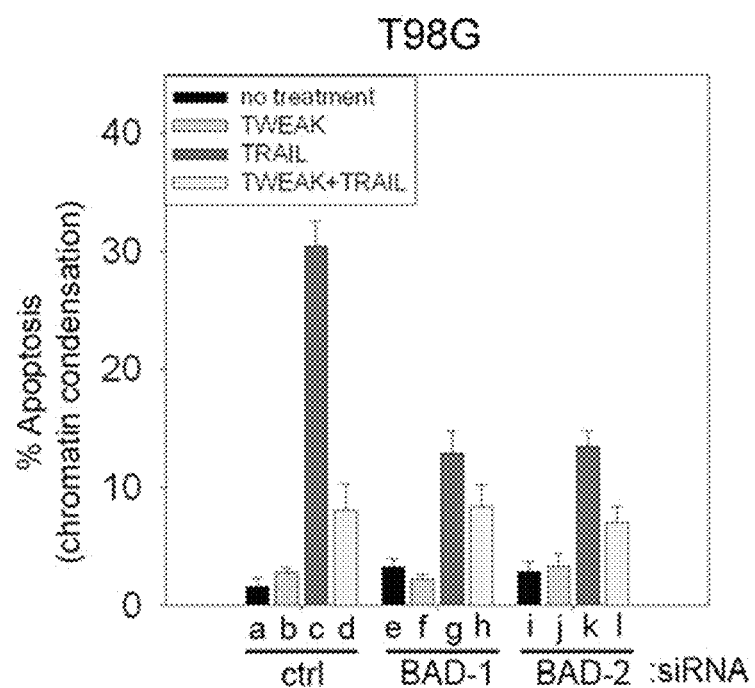
FIG. 22 depicts the percentage of apoptosis in T98G cells treated with TWEAK, TRAIL or TWEAK and TRAIL when BAD expression is suppressed.
Figure 23:
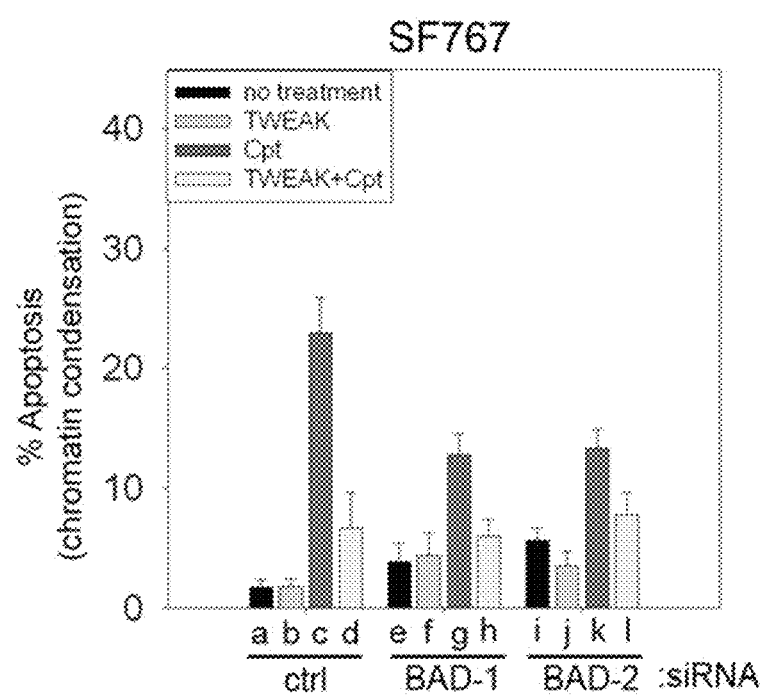
FIG. 23 depicts the percentage of apoptosis in SF767 cells treated with TWEAK, camptothecin, or TWEAK and campothecin when BAD expression is suppressed.

SiRNA-mediated depletion of BAD inhibits cytotoxic- and chemotherapy-induced apoptosis in glioma cells. The expression of BAD was suppressed by transient transfection of siRNA specific to BAD. Transfection of glioma cells with two independent siRNA oligonucleotides showed an 80-95% reduction of BAD protein as compared to no treatment control or control siRNA transfection (FIGS. 20 and 21). Small interfering RNA-mediated suppression of BAD expression antagonized cytotoxic therapy-induced cell death (FIGS. 22 and 23) and chemotherapy-induced cell death (FIGS. 24 and 25) in both T98G and SF767 cells. Pretreatment of glioma cells in which BAD expression was suppressed with TWEAK still protected glioma cells from apoptosis by cytotoxic or chemotherapeutic (FIGS. 24 and 25) agents, similar to TWEAK stimulation in control siRNA transfected glioma cells (FIGS. 22-25.) This suggests that BAD is not the main mediator of the TWEAK protective effect in glioma cells.

Immunohistochemical detection of Akt1, Akt2, and Fn14 on a glioma invasion tissue microarray. Expression levels for Akt1 and Akt2 in relationship to Fn14 were assessed on an invasion glioma TMA consisting of 44 GBM specimen cases assembled to reflect dispersion of infiltrative gliomas. A semi-quantitative scoring system of 0 to 4 for expression levels of each protein was used to reflect the staining intensity in the tumor cells. Examination of Akt1 and Akt2 levels in control non-neoplastic brain specimens from epileptogenic patients showed negative to weak staining, mainly in endothelial cells, neuronal cells, and reactive astrocytes (data not shown). In contrast, expression of both Akt (FIG. 26a and FIG. 26d) and Akt2 (FIG. 26b & FIG. 26e) was present in the GBM specimens and localized in the cytoplasm as well as the nucleus of tumor cells. Further analysis revealed no differences between the staining of Akt1 or Akt2 in the invasive cells compared to the core. However, the distribution of staining intensity between Akt1 and Akt2 among the GBM cases is significantly different ($p<0.05$, chi-squared test; Table 1). The majority of the GBM cases were scored "moderately positive" for Akt1 expression in the core (60.0%) and invasive cells (69.2%) as compared to "strong positivity" discerned in only 33.3% of the core and 23.1% in the rim. In comparison, the staining intensity distribution of Akt2 in the tumor core and invasive cells appears to be more strongly positive, 47.2% (core) and 10 55.6% (rim), while the "moderately positive" scores were identified in 50.0% (core) and 44.4% (rim). Similarly, moderate and strong staining for Fn14 in GBM cells was observed in the tumor core and invading cells in the rim, corroborating previously reported data (FIG. 26c and FIG. 26f) (See Reference 9) The correlation between the expression of Akt1, Akt2, and Fn14 was assessed in the 44 GBM cases. No significant correlation was observed between Akt1 and Akt2. Also, no correlation was observed between Fn14 and Akt1. However, Akt2 protein expression positively correlated with Fn14 expression level ($r=0.31$, $p<0.02$) among the 44 GBM cases (See Table 2).

TWEAK-induced Akt Ser-473 phosphorylation is dependent upon PI3K and Rac1.

TABLE 1

Analysis of Akt1, Akt2, and Fn14 expression levels by IHC on the Glioma Invasion tissue microarray.

| | Percent of Specimens | | | |
|---|---|---|---|---|
| | Negative | Weak | Moderate | Strong |
| Akt1 core | 0.0 | 6.7 | 60.0 | 33.3 |
| Akt1 edge | 0.0 | 11.5 | 69.2 | 19.2 |
| Akt1 rim | 0.0 | 7.7 | 69.2 | 23.1 |
| Akt2 core | 0.0 | 2.8 | 50.0 | 47.2 |
| Akt2 edge | 0.0 | 0.0 | 60.6 | 39.4 |
| Akt2 rim | 0.0 | 0.0 | 44.4 | 55.6 |
| Fn14 core | 0.0 | 5.6 | 47.2 | 47.2 |
| Fn14 edge | 0.0 | 11.5 | 42.3 | 46.1 |
| Fn14 rim | 0.0 | 0.0 | 50.0 | 50.0 |

The values shown are the percentage of cases at each staining intensity. A scoring system of 0 to 4 for the expression level of each protein was used to indicate the staining intensity in the tumor cells. 0 = negative, 1 = weak, 2 = moderate, 3-4 = strong.

TABLE 2

Pearson's Correlation of Akt1, Akt2, and Fn14 Protein expression in glioblastoma multiforme specimens (r = correlation coefficient. Significant p-values are bolded.)

| Antigen 1 | Antigen 2 | r | p-value |
|---|---|---|---|
| Akt1 | Akt2 | 0.07 | 0.59 |
| Akt1 | Fn14 | −0.02 | 0.92 |
| Akt2 | Fn14 | 0.31 | 0.02 |

Figure 2:
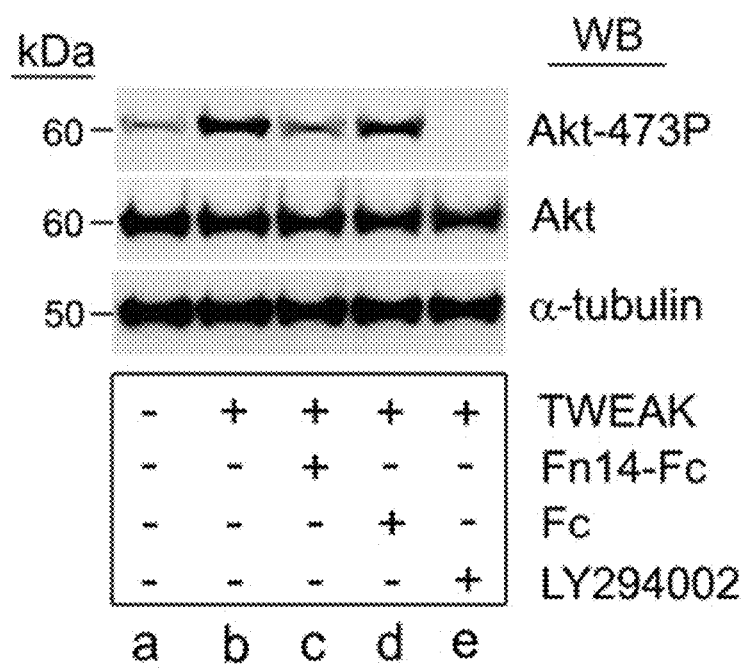
FIG. 2 depicts lysates of T98G cells treated with TWEAK with and without soluble Fn14 and western blotted for total and phosphorylated Akt.
Figure 3:
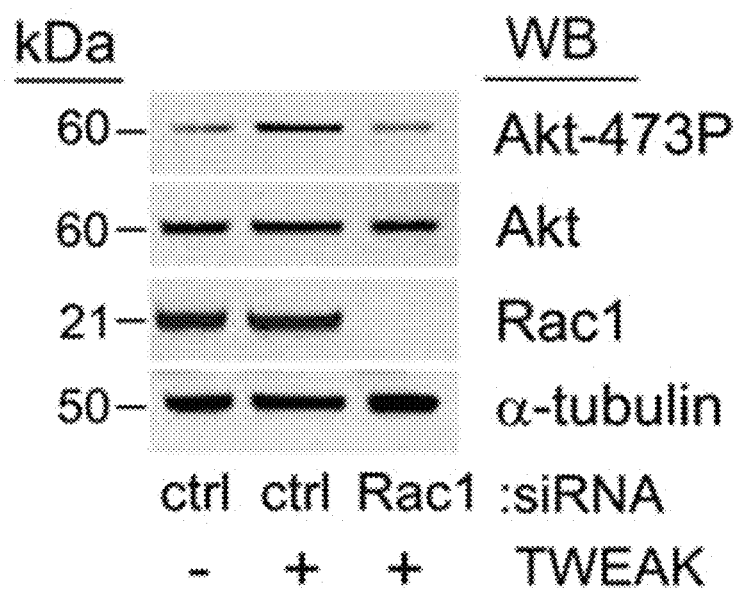
FIG. 3 depicts lysates of T98G cells treated with TWEAK and western blotted for total and phosphorylated Akt as well as Rac1.

Referring now to FIG. 1, T98G and SF767 glioma cells were treated with TWEAK and then harvested at the indicated times. Protein lysates were analyzed by Western blotting using antibodies to Akt Ser-473, total Akt, and α-tubulin. Referring now to FIG. 2, T98G cells were pretreated with TWEAK, with TWEAK that had been preincubated with Fn14 decoy receptor (Fn14-Fc), with TWEAK preincubated with Fc protein, or with LY294002 for 10 minutes prior to TWEAK addition to cells. Total cell lysates were collected after 10 min of TWEAK treatment and analyzed for phosphorylated Akt-473, total Akt, and α-tubulin. Referring now to FIG. 3, T98G cells were transfected with siRNA markering luciferase (negative control) or Rac1 for 24 hours. Cells were treated with TWEAK for 10 minutes and protein lysates were analyzed for phosphorylated Akt-473, total Akt, Rac1 and α-tubulin. Each panel is a representation of three independent experiments.

Figure 4:
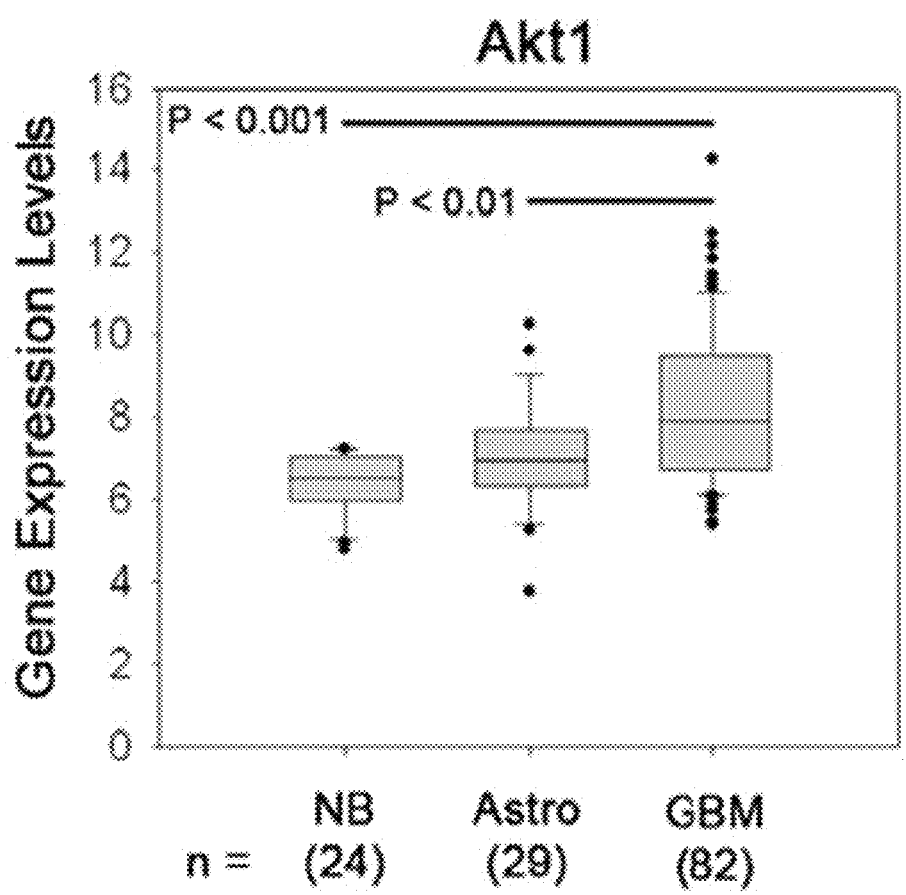
FIG. 4 depicts mRNA expression of Akt1 in brain tissue of the indicated type.
Figure 7:
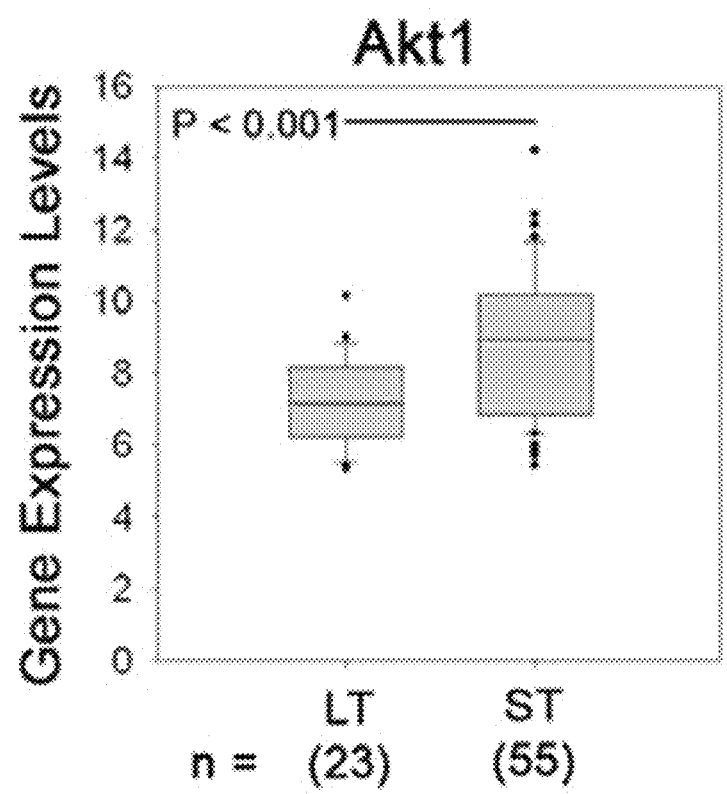
FIG. 7 depicts mRNA expression of Akt1 in long term versus short term survivors of glioblastoma.
Figure 8:
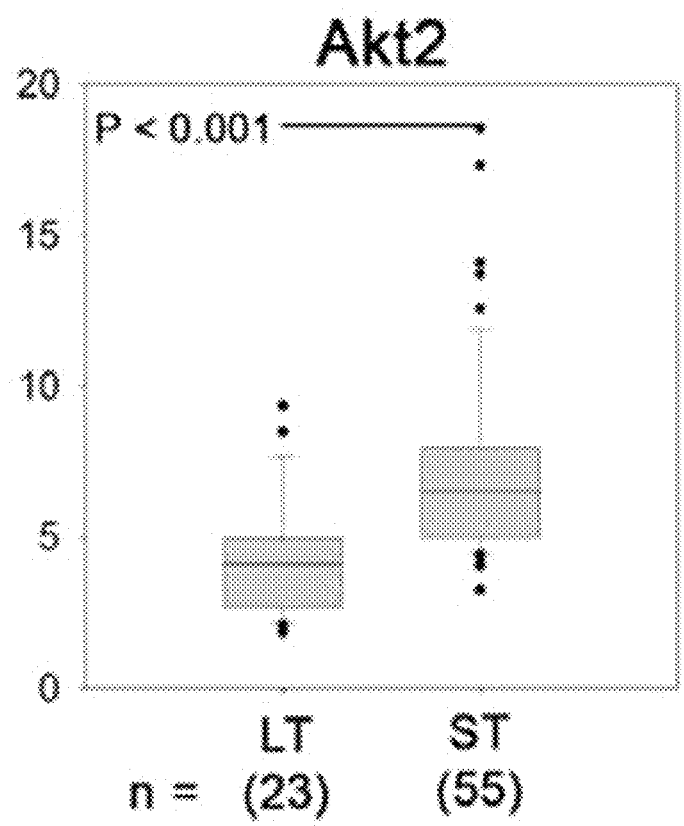
FIG. 8 depicts mRNA expression of Akt2 in long term versus short term survivors of glioblastoma.
Figure 9:
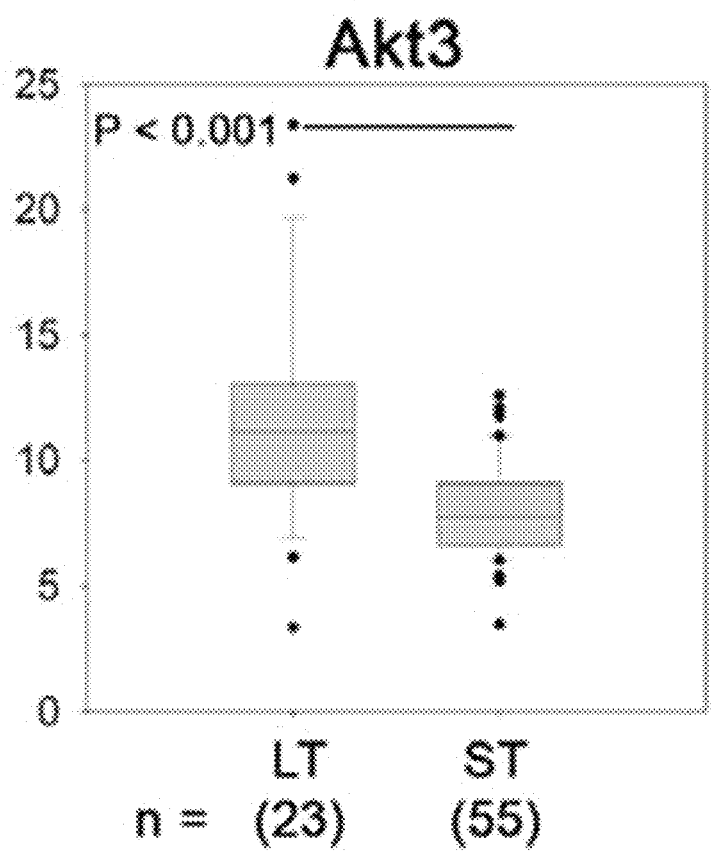
FIG. 9 depicts mRNA expression of Akt3 in long term versus short term survivors of glioblastoma.

Referring now to FIGS. 4, 5, and 6, Gene expression profiling of Akt isoforms across non-neoplastic brain samples and brain tumor samples were performed. mRNA expression levels of Akt1 (FIG. 4), Akt2 (FIG. 5), and Akt3 (FIG. 6) from the NCBI Gene Expression Omnibus GDS1962 dataset are presented as box-and-whisker plots. The box for each gene represents the interquartile range (25-75th percentile) and the line within this box is the median value. Bottom and top bars of the whisker indicate the 10th and 90th percentiles, respectively. Outlier values are indicated (closed circles). Significance between the indicated classes of brain specimens was tested using a two-sample t test assuming unequal variances. (NB=normeoplastic brain; Astro=low grade astrocytomas; GBM=glioblastoma multiforme). Referring now to FIGS. 7, 8, and 9, principal component analysis of brain 10 tumors from NCBI Gene Expression Omnibus GDS1962 dataset revealed two groups differing by their survival and were denoted as long term (LT) survival and short-term (ST) survival. Box-and-whisker plots for Akt1 (FIG. 7), Akt2 (FIG. 8), and Akt3 (FIG. 9) expression in GBM specimens for each cluster are shown. Significance between the two populations was tested with a two-sample t test assuming unequal variances.

Figure 10:
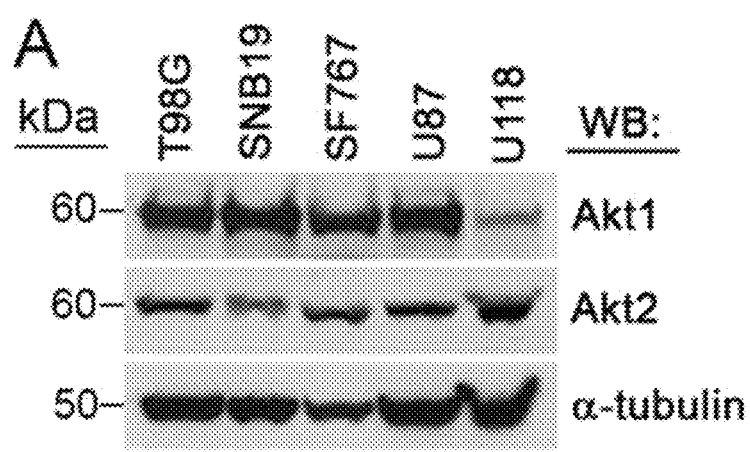
FIG. 10 depicts a western blot showing Akt1 and Akt2 expression in the indicated cell lines.

Akt1 and Akt2 are expressed in glioma cell lines and are phosphorylated in TWEAK stimulated cells. Referring now to FIG. 10: T98G, SNB19, SF767, U87, and U118 cell lysates were analyzed for endogenous levels of Akt1 and Akt2 by Western blotting. To monitor gel loading, α-tubulin protein levels were also analyzed. Referring now to FIG. 11: T98G cells were treated with TWEAK for 10 min. Cell lysates were subjected to immunoprecipitation with Akt1- or Akt2-specific antibodies and then immunoblotted for phospho Akt-473 (HC=heavy chain IgG; LC=light chain IgG). TWEAK stimulation of glioma cell survival depends on Akt2 function. SiRNA specific for Akt1 (FIG. 12) and Akt2 (FIG. 13) suppress expression of Akt1 and Ak2 protein in both. T98G and SF767 glioma cells. Cells were transfected with siRNA oligonucleotides capable of binding control luciferase, Akt1 or Akt2. After 72 hours, protein lysates were collected and analyzed by Western blotting for Akt1, Akt2 and α-tubulin. Each panel is a representation of three independent experiments. In FIGS. 14-17, T98G and SF767 cells were transfected with siRNA specific to control luciferase (ctrl), Akt1, or Akt2. Cells were then cultured in reduced serum for 16 hours prior to treatment with TWEAK (100 ng/ml) alone or TWEAK pre-treatment (100 ng/ml) for 2 hours followed by the addition of TRAIL (100 ng/ml), Camptothecin (1 μM), or TMZ (200 μM). Cells were fixed 24 h later and stained for DAPI. Cells with condensed, fragmented chromatin were manually scored as apoptotic cells. At least 10 fields (total of 1000 cells) were evaluated and data reported as apoptotic cells/total cells×100. The values represent the mean and standard deviation of five replicate measurements.

Figure 19:
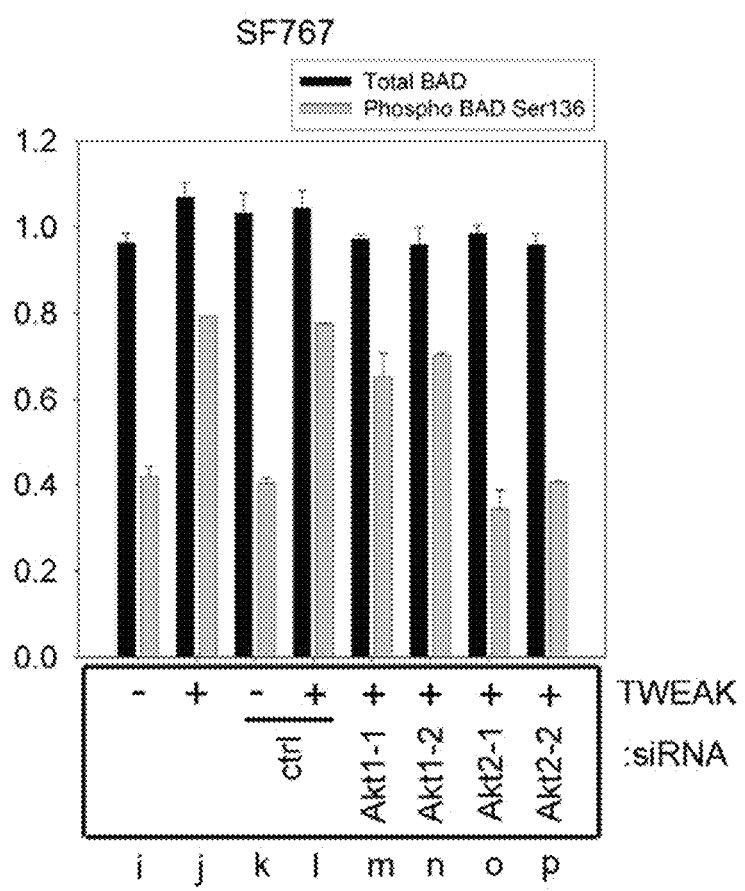
FIG. 19 depicts phosphorylation of BAD in SF767 cells when Akt1 or Akt2 expression is suppressed.
Figure 24:
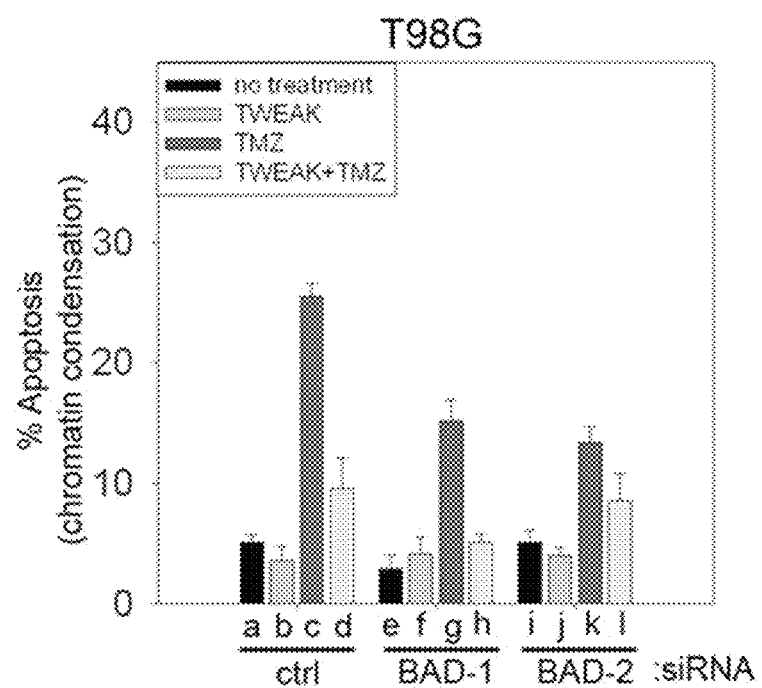
FIG. 24 depicts the percentage of apoptosis in T98G cells treated with TWEAK, temozolimide, or TWEAK and temozolimide when BAD expression is suppressed.
Figure 25:
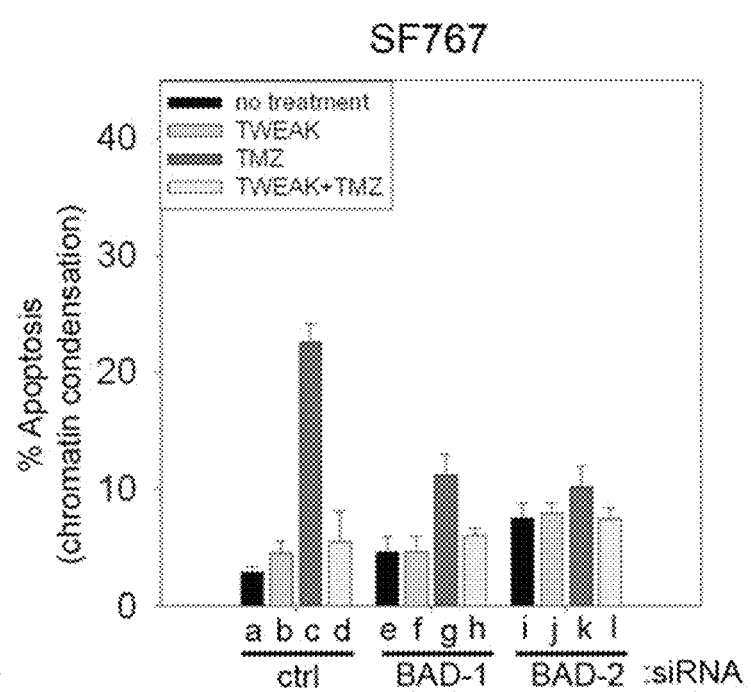
FIG. 25 depicts the percentage of apoptosis in SF767 cells treated with TWEAK, temozolimide, or TWEAK and temozolimide when BAD expression is suppressed.

In FIGS. 18 and 19, TWEAK-induced BAD phosphorylation on serine 136 is dependent upon Akt2 function. T98G (FIG. 18) and SF767 (FIG. 19) glioma cells were transfected with siRNA oligonucleotides markering control luciferase, Akt1 or Akt2. Twenty-four hours later cells were cultured under reduced serum for 16 hours prior to TWEAK addition for 10 minutes. Cellular lysates were collected and analyzed for phosphorylated BAD Ser-136 and total BAD by ELISA. Data represents the mean and standard deviation from three independent experiments with each experiment conducted in triplicate. Depletion of BAD expression protects glioma cells from cytotoxic- and chemotherapyinduced apoptosis. T98G (FIG. 20) and SF767 (FIG. 21) glioma cells were transfected with siRNA oligonucleotides markering control luciferase or BAD. After 72 hours protein lysates were collected and analyzed by Western blotting for BAD and α-tubulin. Each panel is a representation of three independent experiments. T98G and SF767 cells were transfected with siRNA markering either control luciferase (ctrl) or BAD. Cells were then cultured in reduced serum for 16 hours prior to treatment with TWEAK (100 ng/ml) alone or TWEAK pre-treatment (100 ng/ml) for 2 hours followed by the addition of TRAIL (100 ng/ml) (FIG. 22) Camptothecin (1 μM) (FIG. 23), or TMZ (200 μM) (FIGS. 24 and 25). Cells were fixed 24 hours later and stained for DAPI. Cells with condensed, fragmented chromatin were manually scored as apoptotic cells. At least 10 fields (total of 1000 cells) were evaluated and data reported as apoptotic cells/total cells×100. The values represent the mean and standard deviation of five replicate measurements.

Figure 26:
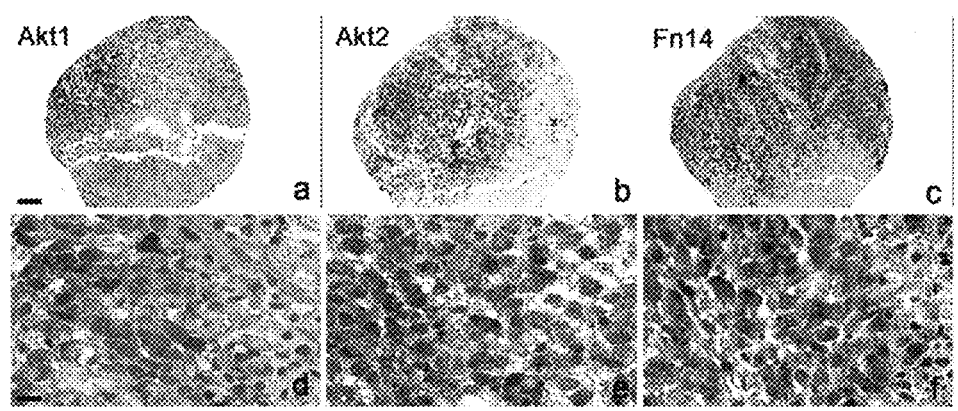
FIG. 26 depicts immunohistochemical detection of Akt1, Akt2, and Fn14 during GBM invasion.

FIG. 26 depicts immunohistochemical detection of Akt1, Akt2 and Fn14 during GBM invasion. Paraffin-embedded, formalin-fixed sections of a glioma invasion tissue microarray were stained with antibodies against Akt1, Akt2 and Fn14. Panels are a representation of staining of Akt1, Akt2, and Fn14 from a single GBM case. Top (a, b, c)×10 magnification (Bar=100 μm). Bottom (d, e, f)×40 magnification (Bar=20 μm).

REFERENCES

So as to reduce the complexity and length of the Detailed Specification, Inventors herein expressly incorporate by reference to the extent applicable, all of the following materials.
1. 2007-2008 Primary Brain tumors in the United States Statistical Report. Central Brain Tumor Registry of the United States Chicago, Ill. (2008).
2. Macdonald D R, Semin Oncol 30 72-76 (2003).
3. Salhia B et al, Expert Rev Mol Diagn, 6, 613-626 (2006).
4. Giese A et al, J Clin Oncol 21, 1624-1636 (2003).
5. Berens M E and Giese A, Neoplasia 10 1, 208-219 (1999).
6. Locksley R M et al, Cell 104, 487-501 (2001).
7. Winkles J A, Nat Rev Drug Discov 7, 411-425 (2008).
8. Tran N L et al, Am J Pathol 162, 1313-1321 (2003).
9. Tran N L et al, Cancer Res 66, 9535-9542 (2006).
10. Brown S A et al, Biochem J 371, 395-403 (2003).
11. Tran N L et al, J Biol Chem 280, 3483-3492 (2005).
12. Datta S R et al, Cell 91, 231-241 (1997).
13. Coffer P J et al, Biochem J 335, 1-13 (1998).
14. Alessi D R and Cohen P, Curr Opin Genet Dev 8, 55-62 (1998).
15. del Peso L et al, Science 278, 687-689 (1997).
16. Cardone M H et al, Science 282, 1318-1321 (1998).
17. Bellacosa A et al, Adv Cancer Res 94, 29-86 (2005).
18. Bellacosa A, et al, Int J Cancer 64 280-285 (1995).
19. Irie H Y et al, J Cell Biol 171, 1023-1034 (2005).
20. Cheng J Q et al, Proc Natl Acad Sci USA 89, 9267-9271 (1992).
21. Yuan Z Q et al, Oncogene 19, 2324-2330 (2000).
22. Altomare D A et al, J Cell Biochem 87, 470-476 (2002).
23. Tanno S et al, Cancer Res 61, 589-593 (2001).
24. Yang Z Z et al, J Biol Chem 278, 32124-32131 (2003).
25. Stahl J M et al, Cancer Res 64, 7002-7010 (2004).
26. Donohue P J et al, Arterioscler Thromb Vasc Biol 23, 594-600 (2003).
27. Tran N L, et al, J Biol Chem 277 32905-32914 (2002).
28. Chuang Y Y et al, Cancer Res 64 8271-8275 (2004).
29. Porstmann T and Kiessig S T, J Immunol Methods 150 5-21, (1992).
30. Kislin K L et al, Neoplasia 11, 377-387 (2009).
31. Mackey T J et al, Urology 52 1085-1090, (1998).
32. Fukuda A, et al, J Bone Miner Res 20, 2245-2253 (2005).
33. Jiang K et al, Blood 101 236-244, (2003).
34. Cheng H L et al, J Biol Chem 275, 27197-27204 (2000).
35. Sun M et al, Cancer Res 61, 5985-5891 (2001).
36. Nakatani K et al, J 10 Biol Chem 274, 21528-21532 (1999).
37. Cicenas J, Int J Biol Markers 23, 1-9 (2008).
38. Fan X, et al, Int J Oncol 21, 1141-50 (2002).
39. Ekert P G et al, Blood 108, 1461-1468 (2006).
40. Feng F, et al, Endocrinology 149, 1505-1513 (2008)
41. Kumar M et al, J Immunol 182, 2439-2448 (2009).
42. Dogra C et al, FASEB J 21, 1857-1869 (2007).

43. Arboleda M J et al, Cancer Res 63, 196-206 (2003).
44. Yuan Z Q et al, J Biol Chem 278, 23432-23440 (2003.)
45. Pu P et al, J Neurooncol 76, 1-11 (2006).
46. Knobbe C B and Reifenberger G, Brain Pathol 13, 507-518 (2003).
47. Hu S et al, Genomics 62, 103-107 (1999).
48. Park J B et al, Neuron 45, 345-351 (2005).
49. Pipsa J et al, Gene Expr Patterns 3 675-679 (2003).
50. Hisaoka T et al, Glia 45, 313-324 (2004).
51. Shao Z et al, Neuron 45, 353-359 (2005).
52. Hisaoka T et al, Brain Res Dev Brain Res 143, 105-109 (2003).
53. Maher E A et al, Genes Dev 15, 1311-1333 (2001).
54. Castro M G et al, Pharmacol Ther 98, 71-108 (2003).
55. Rich J N and Bigner D D, Nat Rev Drug Discov 3, 430-446 (2004).
56. Bredel M et al, J Am Med Assoc 302, 261-275 (2009).
57. Parsons D W et al, Science 321, 1807-1812 (2008).
58. Lesniak M S and Brem H, Nat Rev Drug Discov 3, 499-508, (2004).
59. Tysnes B B and Mahesparan R, J Neurooncol 53, 129-147 (2001).
60. Friedl P and Wolf K, Nat Rev Cancer 3, 362-374 (2003).
61. Joy A M et al, J Cell Sci 116, 4409-4417 (2003).

I claim:

1. A method of identifying a brain tumor as invasive glioblastoma; comprising:
adding a first antibody capable of binding to a marker consisting of SEQ ID NO: 4 to a mixture comprising a sample from the tumor;
subjecting the mixture to conditions that allow detection of the binding of the antibody to the marker; and
classifying the brain tumor as an invasive glioblastoma when the binding of the antibody to the marker in the sample is more than twice the binding of the antibody to a normeoplastic brain sample control.

2. The method of claim 1 wherein the first antibody comprises a first label.

3. The method of claim 2 wherein the first label comprises a fluorescent compound.

4. The method of claim 2 wherein the first label comprises an enzyme.

5. The method of claim 2 wherein the first label comprises a radioisotope.

6. The method of claim 2 wherein the first label comprises a ligand.

7. The method of claim 1 further comprising adding a second antibody to the mixture, wherein the second antibody is capable of binding to the first antibody.

8. The method of claim 7 wherein the second antibody comprises a second label.

9. The method of claim 1 wherein the first antibody is affixed to a solid substrate.

10. The method of claim 9 wherein the conditions comprise microarray analysis.

11. The method of claim 10 wherein the sample comprises a brain biopsy.

12. A method of predicting disease outcome of a patient with glioblastoma comprising:
adding a first antibody capable of binding to a marker consisting of SEQ ID NO: 4 to a mixture comprising a sample from the glioblastoma tumor;
subjecting the mixture to conditions that allow detection of the binding of the antibody to the marker; and
classifying the patient into a cohort of short term survivors when the binding of the antibody to the marker in the sample is more than twice the binding of the antibody to a normeoplastic brain sample control.

13. The method of claim 12 wherein short term survivors are predicted to survive less than 680 days.

14. The method of claim 12 wherein short term survivors are predicted to survive less than 400 days.

* * * * *